(12) United States Patent
Shrestha

(10) Patent No.: US 12,278,013 B2
(45) Date of Patent: Apr. 15, 2025

(54) DEVICE AND METHOD FOR DETERMINING A LEVEL OR CONCENTRATION OF AN ANALYTE IN A PERSON'S BLOOD FROM ONE OR MORE VOLATILE ANALYTES IN THE PERSON'S BREATH

(71) Applicant: Sudhir Shrestha, Rohnert Park, CA (US)

(72) Inventor: Sudhir Shrestha, Rohnert Park, CA (US)

(73) Assignee: SONOMA STATE UNIVERSITY, Rohnert Park, CA (US)

( * ) Notice: Subject to any disclaimer, the term of this patent is extended or adjusted under 35 U.S.C. 154(b) by 685 days.

(21) Appl. No.: 17/508,877

(22) Filed: Oct. 22, 2021

(65) Prior Publication Data
US 2022/0139557 A1 May 5, 2022

Related U.S. Application Data

(60) Provisional application No. 63/109,323, filed on Nov. 3, 2020.

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/0004* (2013.01); *A61B 5/082* (2013.01); *A61B 5/097* (2013.01); *A61B 5/7246* (2013.01); *A61B 5/7267* (2013.01); *G06N 3/08* (2013.01); *G06N 20/10* (2019.01)

(58) Field of Classification Search
CPC ......... G16H 50/20; G16H 40/20; G16H 40/67
See application file for complete search history.

(56) References Cited

U.S. PATENT DOCUMENTS

2006/0239856 A1* 10/2006 Mobley ................. B60R 25/257
422/84
2007/0192134 A1* 8/2007 Littenberg ............. G16H 70/20
600/300

(Continued)

*Primary Examiner* — Jay M. Patel
(74) *Attorney, Agent, or Firm* — Central California IP Group, P.C.; Andrew D. Fortney

(57) ABSTRACT

A device configured to determine a level or concentration of a disease-related analyte in a person's blood from volatile analyte(s) in the person's breath. The device includes one or more sensors configured to detect the volatile analyte(s) in the person's breath, a microcontroller in communication with each sensor, a transmitter, a battery, and a housing. The microcontroller contains logic that correlates parameter values from the sensor(s) or the level/concentration of the volatile analyte(s) to the level/concentration of the disease-related analyte. The transmitter is configured to transmit the parametric value from each sensor and/or the level/concentration of the volatile analyte(s) and/or the disease-related analyte. The housing surrounds, encloses and/or secures the sensor(s), the microcontroller, the transmitter and the battery, and contains a tube or opening through which the person exhales so that the person's breath contacts the sensor(s).

20 Claims, 15 Drawing Sheets

(51) Int. Cl.
  *A61B 5/08*   (2006.01)
  *A61B 5/097*  (2006.01)
  *G06N 3/08*   (2023.01)
  *G06N 20/10*  (2019.01)

(56) References Cited

U.S. PATENT DOCUMENTS

| | | | | |
|---|---|---|---|---|
| 2011/0245634 | A1* | 10/2011 | Ray | A61B 5/1486 |
| | | | | 600/309 |
| 2012/0107862 | A1* | 5/2012 | Harrop | G01N 33/80 |
| | | | | 435/29 |
| 2013/0165900 | A1* | 6/2013 | Braig | A61B 5/150267 |
| | | | | 604/504 |
| 2013/0226605 | A1* | 8/2013 | Miller | G16H 50/20 |
| | | | | 705/2 |
| 2016/0317744 | A1* | 11/2016 | Rule | A61B 5/7275 |
| 2019/0231222 | A1* | 8/2019 | Ahmad | A61B 5/097 |

\* cited by examiner

DEVICE AND METHOD FOR DETERMINING A LEVEL OR CONCENTRATION OF AN ANALYTE IN A PERSON'S BLOOD FROM ONE OR MORE VOLATILE ANALYTES IN THE PERSON'S BREATH

CROSS REFERENCE TO RELATED APPLICATION(S)

This application claims the benefit of U.S. Provisional Patent Application No. 63/109,323, filed on Nov. 3, 2020, incorporated herein by reference as if fully set forth herein.

FIELD OF THE INVENTION

The present invention generally relates to the field(s) of trace component analysis. More specifically, embodiments of the present invention pertain to novel apparatuses for collecting and analyzing data to qualitatively and/or quantitatively determine the amount of a component in a gas-phase sample, and methods of making and using the same.

DISCUSSION OF THE BACKGROUND

Research and development in breath-based diagnosis and monitoring devices for diabetes and other diseases have recently seen an exponential growth. This has created a need in the scientific and R&D communities for a sensor device that allows large-scale breath data collection from patients in real-life situations. This is particularly important as advances in machine learning and artificial intelligence have enabled complex sensor pattern-based recognitions and classifications.

Diabetes is a major health problem in the United States that affects more than 122 million people. Obesity and diabetes mellitus (DM) have been increasing in prevalence and severity at an extreme rate in the United States since the 1990s. In 2000, less than 5% of the US population was diagnosed as having diabetes. According to the U.S. Center for Disease Control (CDC), in 2018, 10.5% of the U.S. population (34.2 million people) had diabetes. Another 88 million people, more than 1 in 3 adults, had prediabetes. When left untreated, prediabetes leads to type 2 DM within five years. The CDC also reported that the estimated cost of diagnosed diabetes was $327 billion.

DM generally requires continual management of blood glucose (BG) to avoid acute and long-term complications. Current self-monitoring of BG is performed primarily using one or more finger-stick glucose measurements daily. However, failure to manage diabetes can lead to acute and long-term complications, including premature death, vision loss, heart disease, kidney failure, and amputation of toes, feet, or legs. It is believed that about half of patients with type-2 diabetes do not adhere to their treatment plan and fail to manage their BG. As a result, diabetes is the seventh leading cause of death in the U.S. Thus, a diabetes monitoring solution that helps and encourages patients to adhere to their treatment plans is urgently needed.

Human exhaled breath contains more than 200 VOCs, many of which have been shown to carry markers of disease. Correlations between breath VOCs and diseases such diabetes, lung cancer, breast cancer, and heart disease are well documented. Sensors that use breath VOCs to detect diseases have also been widely studied. For example, a sensor array was shown to detect lung cancer from breath with up to 86% accuracy. Sensors for detecting breast cancer, colorectal cancer, prostate cancer, diabetes, and asthma from breath have also been reported. However, researchers have struggled to develop actual breath VOC-based diagnostic tests. The lack of success in developing clinically applicable diagnostic solutions have primarily been due to two critical barriers (as discussed herein).

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

The present sensor device has a small form-factor (e.g., is handheld) and can take breath input, record sensor readings, and wirelessly send data to the cloud. The device is easy to use and can be given to the patients to conduct self-tests at home. The device has three or more slots for chemical/volatile organic compound (VOC) sensors (which can be expanded as needed), a sensor interface that can be programmed to match the sensor characteristics, and a program for automatic calibration of the sensors. The device comes with three VOC sensors, which in some cases can be exchanged for different sensors, based on patient/study needs. The device may have a display and/or data input keys for entering information (e.g., patient information, such as name, a password, etc.) and health data (e.g., fasting, before meal, after meal, exercise, running, etc.). The device can be easily programmed to package and format the data, then send it to the cloud for automatic logging (e.g., entry and storage) in a cloud database. The microcontroller (MCU) in the device can be (re)programmed with trained algorithms for real-time classification of patient breath data, and can make analyses and predictions based on the patterns and/or classification of the data. Thus, this device can be used for verification and further training of the algorithm, as well as implementing the trained algorithms and monitoring and/or diagnosing patient wellness/illness, without any hardware (e.g., electronics, such as MCU) modifications.

Thus, the present invention relates at least in part to a device, comprising one or more sensors configured to determine one or more volatile analytes in a person's breath; a microcontroller in communication with each of the one or more sensors, configured to receive a parametric value from each of the one or more sensors; a transmitter configured to transmit at least one of (1) the parametric value from each of the one or more sensors, (2) the level or concentration of the one or more volatile analytes in the person's breath, and (3) the level or concentration of a disease-related analyte in the person's blood to at least one of an external data processing device and a display; a battery configured to provide electrical power to the one or more sensors, the microcontroller, and the transmitter; and a housing that surrounds and/or encloses the one or more sensors, the microcontroller, the transmitter and the battery, or at least secures the one or more sensors, the microcontroller, the transmitter and the battery in place relative to one another. The microcontroller contains logic adapted to correlate (i) the parametric value from the one or more sensors or (ii) the level or concentration of the one or more volatile analytes in the person's breath (e.g., when the correlation of the parametric value[s] from the sensor[s] to the level or concentration of the volatile analyte[s] in the person's breath is known) to the level or concentration of a disease-related analyte in the person's blood. The housing contains or secures a tube or opening through which the person exhales so that the person's breath contacts the one or more sensors for a predetermined minimum period of time. In one embodiment, the person has diabetes (e.g. diabetes mellitus), or one of more symptoms or conditions associated with diabetes, the disease-related analyte is glucose, and the sensors may detect acetone and ethanol.

In some embodiments, the device further comprises a support vector machine or artificial neural network that, when executed by the microcontroller, correlates the parametric value from the one or more sensors or the level or concentration of the one or more volatile analytes in the person's breath with known levels or concentrations of the disease-related analyte in the person's blood. For example, the support vector machine or artificial neural network may be stored in a first memory within the housing, and accessible and executable by the microcontroller.

In most embodiments, the housing comprises a first chamber that encloses the one or more sensors, a second chamber that surrounds and/or encloses the microcontroller and the transmitter, and a wall, barrier or partition that separates the first chamber from the second chamber. In general, the chamber within the housing into which the person exhales is separate from the chamber(s) that house or protect the electronics. In some further embodiments, the first chamber has a wall with one or more openings or vents therein, for the person's breath to exit or escape from the first chamber. The present device may further comprise a circuit board in the housing, mechanically supporting the sensor(s), the microcontroller and the transmitter. The circuit board may have a plurality of traces thereon, electrically connecting (i) each sensor to the microcontroller and (ii) the microcontroller to the transmitter.

In some embodiments, the device comprises a plurality of the sensors, each configured to detect (i) a different volatile analyte or (ii) at least one of the one or more of the volatile analytes in a different manner from the other sensor(s). For example, when the disease-related analyte is glucose, the plurality of the sensors detect acetone and ethanol. However, in various embodiments, the sensor(s) may detect acetone, ethanol, methyl nitrate, isoprene, propane, benzene, methanol, ethyl benzene and/or carbon monoxide. In such embodiments, the device may further comprise a plurality of analog-to-digital converters (ADCs) corresponding to (e.g., in a 1:1 relationship with) the plurality of sensors. Each ADC converts an analog signal from a corresponding one of the sensors to a digital signal, and the microcontroller receives the digital signal(s) from each of the ADCs.

In many embodiments, the device further comprises a user interface configured to communicate at least a status of the device to the person. The user interface may be as simple as a light emitting diode (LED), which can communicate the status of the device by turning (and staying) on, turning (and staying) off, or flashing (e.g., in a predetermined pattern) to show respective "on" (e.g., warming up or calibrating), "off" (e.g., powered down), and "active testing" (e.g., running a test on a person's breath) states. Alternatively, the user interface may comprise a liquid crystal display (LCD), an electrochromic display, or a touch screen, any of which can display alphanumerical messages, and the latter of which can receive an input from the user.

In certain embodiments, the present device has dimensions, and optionally a mass, enabling the device to be held in the person's hand. For example, the device may have a total mass of less than 1 kg (e.g., ≤500 g, ≤300 g, or any other maximum value <1 kg).

In some embodiments, the device may further comprise (i) a port in the housing, configured to receive a voltage or current, and (ii) a battery recharging circuit, configured to receive the voltage or current and recharge the battery using the voltage or current. For example, the port may be a universal serial bus (USB) port. In some such examples, the device may also receive data and/or instructions (e.g., firmware updates, instructions to upload data, etc.) through the USB port. In some embodiments, the present device may further comprise a receiver configured to wirelessly receive data, instructions or information from an external device, such as a computer or work station in a medical office or hospital.

In some embodiments, the device may further comprise a memory configured to store readings or outputs from each of the one or more sensors during testing of the person's breath. The memory may also store the correlation(s) between the parametric value(s) from the sensor(s) and the level or concentration of the volatile analyte(s) in the person's breath, and/or between the level or concentration of the volatile analyte(s) in the person's breath and the level or concentration of the disease-related analyte in the person's blood (e.g., in the form of one or more look-up tables).

Another aspect of the present invention relates to a method of determining a level or concentration of a disease-related analyte in a person's blood, comprising the person exhaling through a tube or opening in a housing of a device, detecting one or more volatile analytes in the person's breath using one or more sensors in the device, either (i) determining a level or concentration of the volatile analyte(s) in the person's breath, and correlating the level or concentration of the volatile analyte(s) in the person's breath to the level or concentration of the disease-related analyte in the person's blood, or (ii) correlating a parametric reading from the sensor(s) to the level or concentration of the disease-related analyte in a the person's blood, using a microcontroller in the housing and in communication with each sensor, and displaying the level or concentration of the disease-related analyte on a user interface (e.g., in at least one of an external data processing device and a display). The housing is configured so that the person's breath contacts the sensor(s) for a predetermined minimum period of time. A transmitter in the housing and in communication with the microcontroller may transmit the parametric value(s) and/or the level or concentration of the disease-related analyte to the user interface.

In some embodiments, the method further comprises training the microcontroller to correlate the parametric values from the sensor(s) or the levels or concentrations of the volatile analyte(s) in the person's breath with known levels or concentrations of the disease-related analyte in the person's blood. In other or further embodiments, training the microcontroller further comprises correlating known levels or concentrations of the volatile analyte(s) to steady-state or equilibrium readings (i.e., parametric values) of or from the sensor(s). Alternatively, the levels or concentrations of the volatile analyte(s) in the person's breath may be correlated with levels (e.g., high, low, normal) or concentrations of the disease-related analyte in the person's blood using known, reliable data (e.g., from a medical or other scientific study). All such training may be conducted using machine learning (e.g., a support vector machine or an artificial neural network).

As for the present device, in the present method, the person may have diabetes, and the disease-related analyte may be glucose. Similarly, in the present method, the housing may comprise a first chamber that encloses the sensor(s), a second chamber that surrounds and/or encloses the microcontroller and the transmitter, and a wall, barrier or partition that separates the first chamber from the second chamber. In some embodiments, the tube or opening is in fluid communication with the first chamber, and the method further comprises removing the person's breath from the first chamber or allowing the person's breath to pass through a second opening (e.g., a vent) in the first chamber.

In some embodiments of the method, a plurality of the volatile analytes in the person's breath are determined using a plurality of the sensors. Each of the sensors may be configured to detect (i) a different volatile analyte or (ii) at least one of the volatile analytes in a different manner from the other sensor(s). For example, when the method uses a plurality of sensors, the method may comprise detecting acetone and ethanol. However, in various embodiments, the sensor(s) may detect methyl nitrate, isoprene, propane, benzene, methanol, ethyl benzene and/or carbon monoxide, instead of or in addition to acetone and/or ethanol.

In some embodiments, the method may further comprise converting an analog signal from one of the sensors to a digital signal using a corresponding analog-to-digital converter (ADC), and receiving the digital signal in the microcontroller from each corresponding ADC. When a plurality of sensors are present, a corresponding plurality of ADCs may also be present (e.g., in a 1:1 relationship).

In some embodiments, the method further comprises communicating at least a status of the device to the person using a user interface. As for the present device, in the present method, the user interface may comprise a light emitting diode (LED), a liquid crystal display (LCD), an electrochromic display or a touch screen.

In certain advantageous embodiments, the method further comprises holding the device in a hand of the person. In other or further embodiments, the method may further comprise charging a battery in the device using a voltage or current received through a port in the housing, and/or receiving data, instructions or information in the microcontroller from an external device (e.g., through the same port, or wirelessly, using an antenna and a receiver). In some embodiments, the method may further comprise storing readings or outputs from each of the sensors during testing of the person's breath in a memory in the device.

Yet another aspect of the present invention relates to a method of making a device configured to determine a level or concentration of a disease-related analyte in a person's blood from one or more volatile analytes in the person's breath, comprising operably connecting one or more sensors configured to detect the volatile analyte(s) in the person's breath to a microcontroller configured to correlate either (i) a parametric value from the sensor(s) or (ii) the level or concentration of the volatile analyte(s) in the person's breath to the level or concentration of the disease-related analyte in the person's blood, operably connecting a transmitter to the microcontroller, and forming a housing having a tube or opening therein configured so that the person's breath contacts the one or more sensors for a predetermined minimum period of time. The transmitter is configured to communicate the parametric value and/or the level or concentration of the disease-related analyte in a person's blood to at least one of an external data processing device and a display. The housing is configured to contain or secure the one or more sensors, the microcontroller, and the transmitter.

A still further aspect of the present invention relates to a non-transitory computer-readable medium, implementable and/or executable in a computing device equipped with a digital signal processor or microcontroller, containing a set of instructions which, when executed by the digital signal processor or microcontroller, is configured or adapted to perform the present method. Thus, in further embodiments of the computer-readable medium, the set of instructions may further contain one or more instructions which, when executed by the digital signal processor or microcontroller, is/are configured or adapted to perform one or more further embodiments of the present method.

This invention utilizes volatile organic compound (VOC) signatures in the breath of diabetes patients (including patients with type 2 diabetes) using chemical sensors in a handheld sensor device to collect and wirelessly transmit such breath sensor data in real-life situations. The device may use trained machine learning software implemented on the device to process the data. The invention enables a smart sensor device that can estimate BG states and/or values from patient breath, give patients whose conditions can be monitored via exhalations (such as those having type 2 diabetes) an accessible modality to receive instant readings (in the case of diabetes patients, without invasive techniques such as finger pricks), test as many times as they desire, and easily monitor their history, which can help address therapeutic nonadherence and improve patient wellbeing.

DETAILED DESCRIPTION

Figure 1:
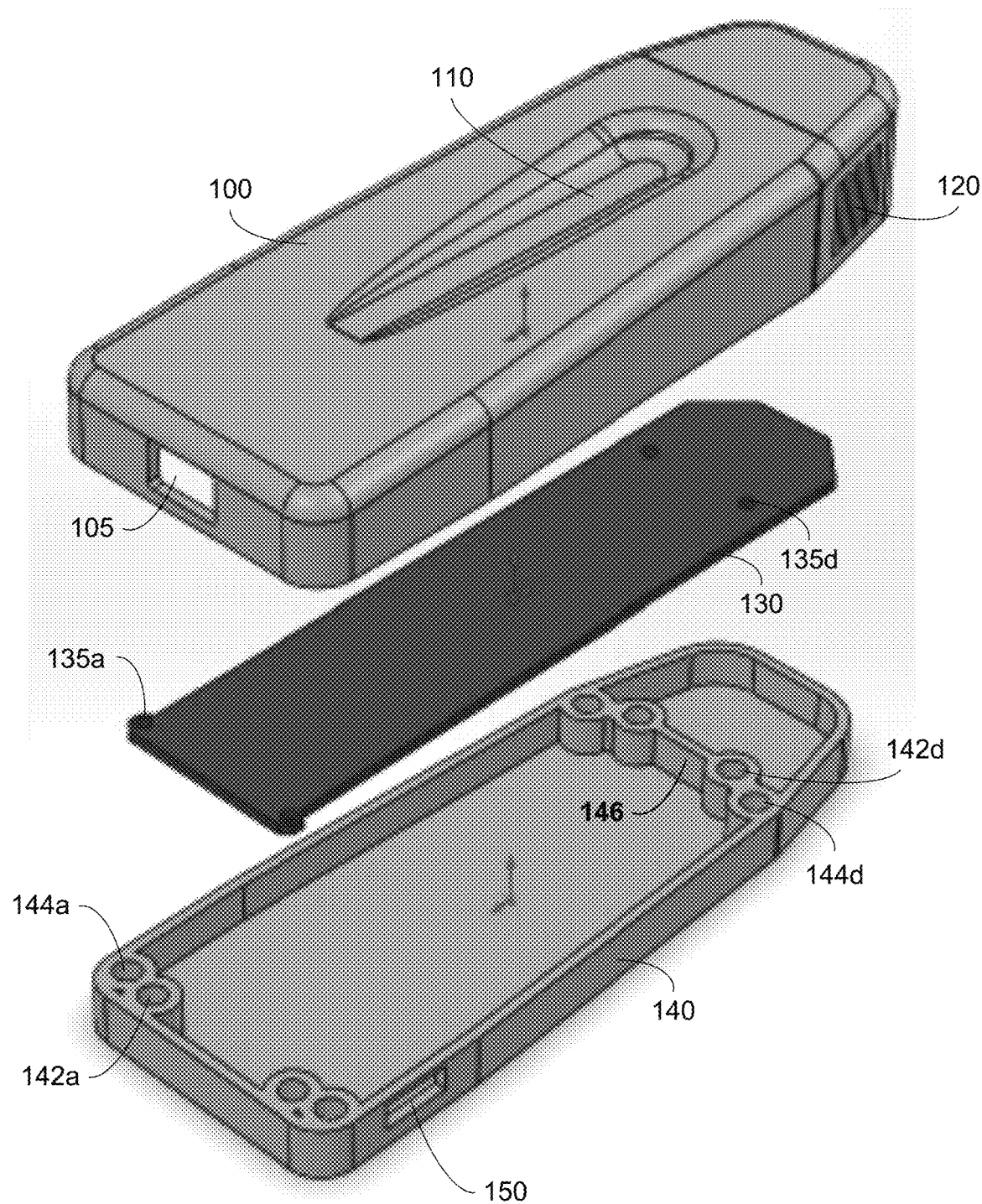
FIG. 1 is an exploded drawing showing an exemplary housing/casing design for the present device.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures and components have not been described in detail so as not to unnecessarily obscure aspects of the present invention. Furthermore, it should be understood that the possible permutations and combinations described herein are not meant to limit the invention. Specifically, variations that are not inconsistent may be mixed and matched as desired.

Some portions of the detailed descriptions which follow are presented in terms of processes, procedures, logic blocks, functional blocks, processing, and other symbolic representations of operations on code, data bits, data streams or waveforms within a computer, processor, controller and/or memory. These descriptions and representations are generally used by those skilled in the data processing arts to effectively convey the substance of their work to others skilled in the art. A process, procedure, logic block, function, process, etc., is herein, and is generally, considered to be a self-consistent sequence of steps or instructions leading to a desired and/or expected result. The steps generally include physical manipulations of physical quantities. Usually, though not necessarily, these quantities take the form of electrical, magnetic, optical, or quantum signals capable of being stored, transferred, combined, compared, and otherwise manipulated in a computer or data processing system. It has proven convenient at times, principally for reasons of common usage, to refer to these signals as bits, waves, waveforms, streams, values, elements, symbols, characters, terms, numbers, or the like, and to their representations in computer programs or software as code (which may be object code, source code or binary code).

It should be borne in mind, however, that all of these and similar terms are associated with the appropriate physical quantities and/or signals, and are merely convenient labels applied to these quantities and/or signals. Unless specifically stated otherwise and/or as is apparent from the following discussions, it is appreciated that throughout the present application, discussions utilizing terms such as "processing," "operating," "computing," "calculating," "determining," "manipulating," "transforming" or the like, refer to the action and processes of a computer or data processing system, or similar processing device (e.g., an electrical, optical, or quantum computing or processing device or circuit), that manipulates and transforms data represented as physical (e.g., electronic) quantities. The terms refer to actions and processes of the processing devices that manipulate or transform physical quantities within the component(s) of a circuit, system or architecture (e.g., registers, memories, other such information storage, transmission or display devices, etc.) into other data similarly represented as physical quantities within other components of the same or a different system or architecture.

For convenience and simplicity, the terms "part," "portion," and "region" may be used interchangeably but these terms are also generally given their art-recognized meanings. Also, unless indicated otherwise from the context of its use herein, the terms "known," "fixed," "given," "certain" and "predetermined" generally refer to a value, quantity, parameter, constraint, condition, state, process, procedure, method, practice, or combination thereof that is, in theory, variable, but is typically set in advance and not varied thereafter when in use. Furthermore, in the context of this application, the terms "wire," "wiring," "line," "signal," "conductor" and "bus" refer to any known structure, construction, arrangement, technique, method and/or process for physically transferring a signal from one point in a circuit to another.

Similarly, for convenience and simplicity, the terms "clock," "time," "timing," "rate," "period" and "frequency" are, in general, interchangeable and may be used interchangeably herein, but are generally given their art-recognized meanings. Also, for convenience and simplicity, the terms "data," "data stream," "waveform" and "information" may be used interchangeably, as may the terms "connected to," "coupled with," "coupled to," and "in communication with," (which may refer to direct or indirect connections, couplings, or communications) but these terms are generally given their art-recognized meanings herein. In addition, a "level" (e.g., of an analyte or a volatile compound) may refer to an estimated amount or concentration, a more generic amount or concentration (e.g., "low," "normal" or "high"), or an amount or concentration above or below a predetermined threshold.

The present small form-factor, handheld sensor device can take breath input, record sensor readings, and wirelessly send data to the cloud. The device is easy to use and can be given to patients to conduct self-tests at home.

One objective of the present invention is to provide a non-invasive and accessible blood glucose (BG) monitoring solution using volatile organic compounds (VOCs) in the breath of patients with type 2 diabetes mellitus (DM). The present sensing device estimates blood glucose states (normal, low, high) from a patient's breath. Machine learning models are trained to accurately classify BG states from patient breath using sensor data collected in real-life situations. In part, the present invention correlates breath sensor readings to finger-stick BG measurements through test data from patients with type 2 diabetes collected in real-life situations. The present sensor device advantageously uses a trained machine learning software model that accurately classifies breath sensor readings into low, normal, and high blood glucose states or groups. Machine learning algorithms such as support vector machines or artificial neural network may be trained using labeled sensor breath data and implemented on the sensor device. In some embodiments, a user interface on the device can be used to input finger-stick BG measurements and display BG states, and a companion smartphone application can monitor and track BG readings taken by the patient and transmitted to medical professionals. Such a solution gives type 2 diabetes and other patients an accessible modality to receive instant status readings (e.g., BG status) without the need for invasive testing (e.g., finger pricks), an ability to test as many times as they desire, and easily monitor their relevant medical history. The present invention is transformative to patient care, because diabetes and other chronic conditions require continual management (e.g., of blood glucose levels). The present invention can help reverse nonadherence to continuous monitoring and management needs.

Furthermore, the method of using the present sensor device to collect data from patients in real-life situations and process the data using trained machine learning models is novel. It may represent a paradigm shift in the way breath-based diagnostic solutions are created, tested and implemented.

The present invention addresses disease monitoring nonadherence with a non-invasive monitoring solution using breath volatile organic compounds (VOCs) that allows patients to monitor their condition as frequently as they desire. In the case of diabetes patients, they may test their BG using the present device between or in place of prescribed finger-stick measurements to easily monitor their BG status throughout the day and over time. By improving adherence to diabetes intervention and treatment, the invention may save millions of lives, improve patients' wellbeing, and save billions of dollars in medical costs related to DM complications.

Studies have reported breath VOC biomarkers of diabetes and other medical conditions. This enables the present non-invasive glucose monitoring device using patient breath data.

Previous attempts in developing sensors to predict BG from breath have faced two significant roadblocks. First, the VOC sensors may degrade and/or may be unstable, and the manufacturing thereof is typically complex. Second, it is difficult to map or correlate chemical analyses and test results to human breath in real-life situations.

Outstanding results using commercially available VOC sensors, and recent advances in machine learning techniques and embedded computing, resulted in use of data collected from commercially available sensors in real-life situations to train machine learning software models to accurately classify BG status from patient breath.

Specifically, correlations between finger-stick BG measurements and breath sensor readings from test data from patients with type 2 diabetes collected in real-life situations can be determined. The present sensor device may have a design similar to a conventional blood alcohol breathalyzer, including a plurality (e.g., three or more) commercial VOC sensors. The present sensor device may further include sufficient computing and wireless transmission capabilities (e.g., a microcontroller, a transmitter IC and an antenna) for automated data logging in a cloud-based data storage system. The physiological parameter being monitored (e.g., BG) may be classified into low, normal, and high groups or states. The correlations between the physiological parameter (e.g., BG) and breath sensor data can be made using conventional statistical analysis.

In addition, the trained machine learning software model in the present device accurately classifies breath sensor readings into a plurality of groups or states (e.g., low, normal, and high). BG and other sensor data can be collected and classified as low, normal, or high using a conventional machine learning algorithm, such as a support vector machine (SVM). The trained software classifies sensor data into low, normal or high states. The software model is implemented on the microcontroller in the sensor device. In each patient breath test, the device classifies the breath sensor readings into a BG state. The results and sensor responses are sent to the cloud.

The present invention thus uses (1) statistically significant correlations between breath sensor tests conducted in real-life situations and corresponding finger-stick BG or other conventional measurements and (2) a machine learning algorithm that is able to classify different physiological states with sufficiently high accuracy in a hand-held device to predict a patient physiological state from the patient's breath. Furthermore, the present invention advances knowledge in the field and provides researchers with a novel approach for using breath VOC data. It may represent a paradigm shift in the way breath-based diagnostic solutions are created and tested (e.g., towards non-invasive blood glucose monitoring techniques, for using breath volatile organic compounds to develop machine learning models using sensors in real-life situations, etc.).

However, previous attempts in developing sensors to estimate BG from breath have faced two critical barriers. The first barrier is the degradation, instability, and manufacturing complexity of sufficiently accurate VOC sensors, and the second is the difficulty in mapping or correlating chemical analyses using known good testing procedures to test results obtained from human breath in real-life situations. The present invention overcomes these barriers using commercially available sensors, collecting breath sensor data from patients in real-life situations, and classifying the data using one or more trained machine learning algorithms.

Referring to the Figures, the device 300 can be recharged by plugging any universal serial bus (USB) cable (e.g., a mini- or micro-USB cable) into a corresponding port (e.g., mini-USB port 235 or micro-USB port 230). The device 300 may be operated up to about one week (e.g., 50 or more tests) on a single charge of the battery 210.

FIG. 1 shows a computer-aided design (CAD) rendering of the device, showing a top or cap section 100 of the housing, a bottom or base section 140 of the housing, and a printed circuit board (PCB) 130 configured to fit between the top and bottom sections 100 and 140. In one example, the exterior of the device 300 is approximately 1" (2.5 cm)×2" (5.0 cm)×4" (10 cm), but other dimensions are also suitable (e.g., a height of 1-10 cm, a width of 2-15 cm, and a length of 3-20 cm). Holes 142*a-d* in the bottom or base section 140 support the PCB 130 and receive screws (not shown) that, when inserted through holes 135*a-d*, secure the board 130 thereto. The holes 144*a-d* in the bottom or base section 140 receive screws (not shown) that secure the top section 100 to the bottom or base section 140.

The sensor device 300 has three slots 132*a-c* for chemical/volatile organic compound (VOC) sensors, which can be easily expanded as needed. Thus, the device 300 includes three or more metal oxide semiconductor (MOS) VOC sensors 270, which can be easily switched with other sensors to match specific patient and/or study needs. For example, the volatile organic compounds (VOCs) in human breath that are biomarkers of diabetes may include acetone, ethanol, methyl nitrate, isoprene, propane, benzene, methanol, ethyl benzene and carbon monoxide. Correlations between these VOCs and BG level or state have been widely reported. This enables use of breath VOCs for non-invasive glucose monitoring.

The device 300 may include an 8-bit or wider microcontroller unit (MCU), such as a 32-bit low-power ARM® Cortex® MCU (commercially available from a number of sources) on a controller PCB 204, a global system for mobile/third generation (GSM/3G) chip 220 that supports multiple cellular bands, a rechargeable lithium ion polymer battery 210, a charging module, an antenna printed circuit board (PCB) 206 with an RF antenna (not shown) thereon, connected to the controller PCB 204 and/or GSM/3G chip 220 through a separate radio frequency (RF) cable 208, and a sensor interface circuit including a power transistor 255 configured to provide power to heat and/or operate the sensors 270. The MCU on the PCB 204 is also commercially available.

The MCU may include a plurality (e.g., 2-10, and in one example, seven) analog-to-digital converters (ADCs) and a plurality of (e.g., ≥2, ≥3, ≥4, etc.) digital input/output (I/O) pins. In one example, the MCU includes 8 I/O pins. The device 300 may further include a subscriber identification module (SIM) card slot and a corresponding card that allows data transmission from the device 300 to a cloud server using cellular towers. For example, the SIM card may comprise a global system for mobile/third generation (GSM/3G), GSM/fourth generation (GSM/4G) or GSM/fifth generation (GSM/5G) chip that supports multiple cellular bands. Such SIM cards are commercially available from Twilio Inc.

The device 300 may also include a multicolor light emitting diode (LED) 250 that can guide the user through the testing process (e.g., using different colors to communicate different information, such as yellow or red to mean "wait" and green to mean "ready for use"). Alternatively, the LED 250 may be a single-color LED, and different information can be communicated using different patterns (such as flashing for "wait," or solid [continuously on] for "ready"). A further alternative may include a display (e.g., an LCD, electrochromic or touch screen display) to show information to the patient and an input pad (or the touch screen display) for the user to input data. In some embodiments, the device 300 includes a buzzer to alert the user (e.g., when calibration and/or initialization is complete) and assist through the testing process (e.g., to notify the user when the time period for exhaling or blowing through the sensor is complete).

Figure 5A:
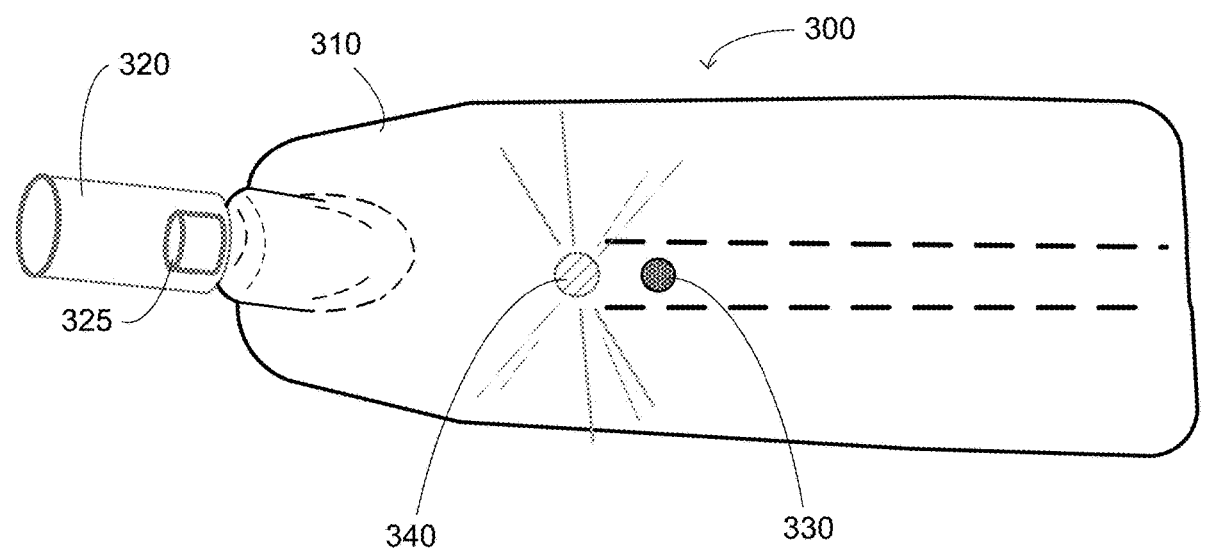
FIGS. 5A-B are top and side views of an exemplary handheld breath data-collecting device in accordance with the present invention.
Figure 5B:
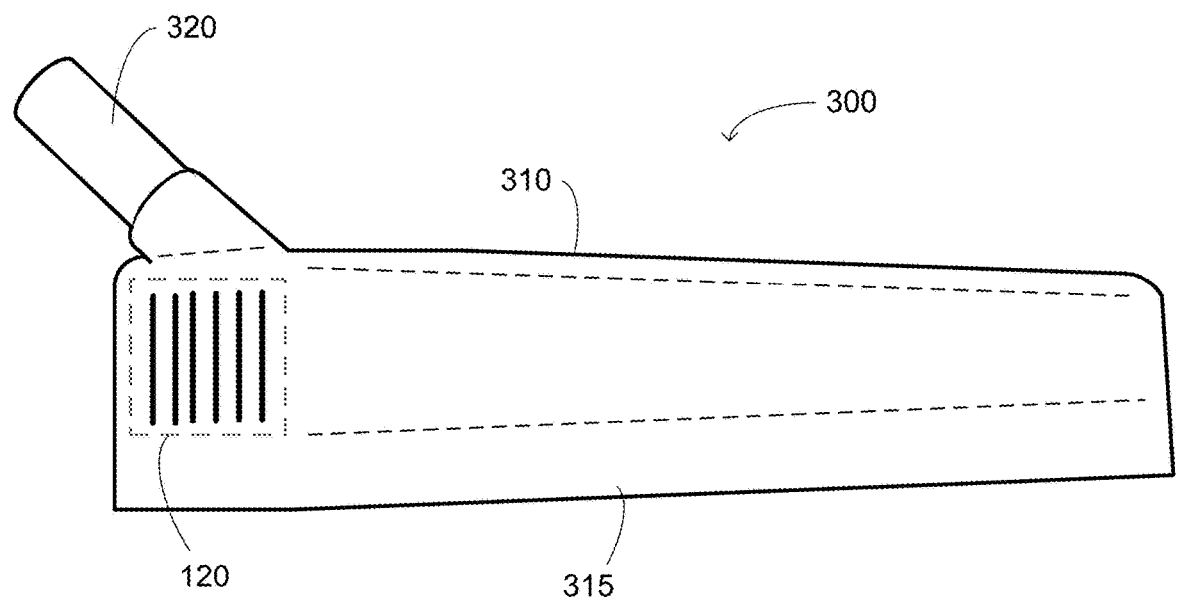

One housing 100-140 for the device is shown in FIG. 1, and an alternative housing (comprising upper and lower sections 310 and 315) is shown in FIG. 5B. One end of each housing is tapered with an opening 325 (FIG. 5A) for the breath to enter the housing for exposure to the sensors 270. A short breathing tube 320 is attached to the opening 325 into which the patient exhales. The opening 320 leads to a chamber (not shown) in the tapered end of the upper section 100/310 of the housing where the three sensors are located. This chamber is isolated from the non-sensor electronic circuitry by a wall or barrier (not shown) in the upper section 100/310 of the housing corresponding to the wall/barrier 146 in the lower section 140 (FIG. 1). The opposite end of the device 300 has an opening 105 for a mini- or micro-USB port 235 to charge and/or program the device 300. User input can also be provided to the device 300 using a mobile device with a touch screen (such as a mobile phone or pad computer) connected to the device 300 through a mini- or micro-USB cable plugged into the port 235.

Figure 6A:
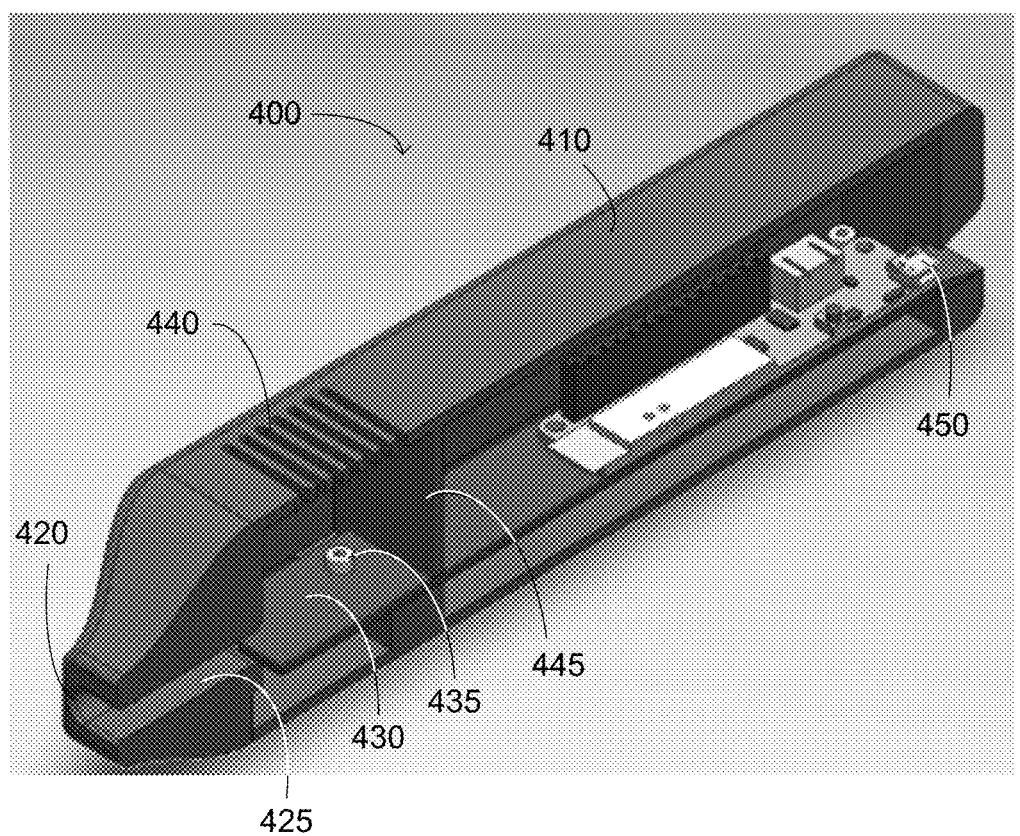
FIGS. 6A-B are perspective and exploded views of another exemplary handheld breath data-collecting device in accordance with the present invention.
Figure 6B:
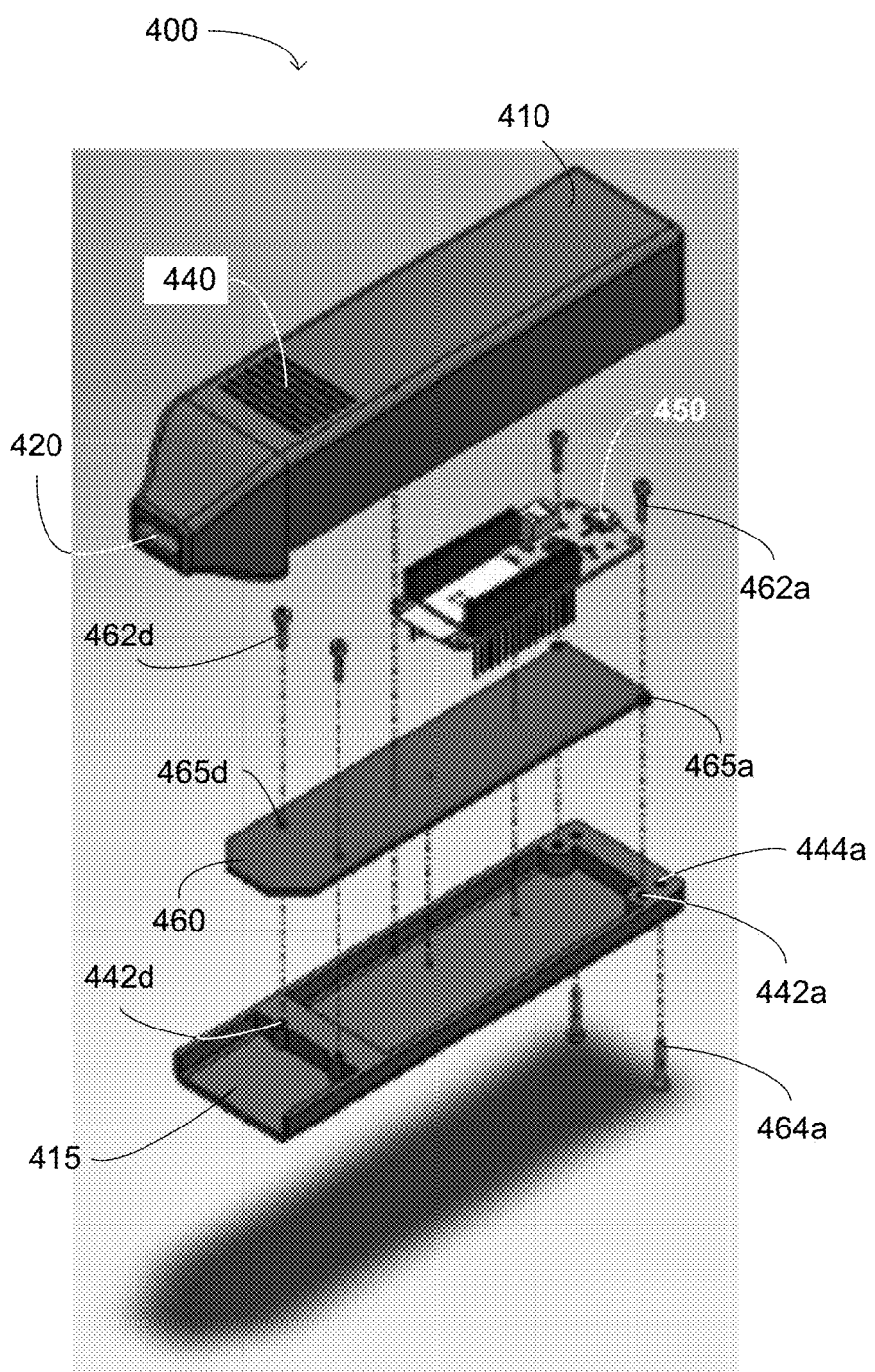

An alternative device 400 and housing 410 are shown in FIGS. 6A and 6B. One end of the device 400 is tapered with an opening 420 for the breath to enter to the sensors. A short breathing tube 425 in fluid communication with the opening 420 allows patients to breath into the device. The opening 420 and tube 425 leads to a chamber 430 where the sensor(s) 435 is/are placed. The patient's exhalation exits the chamber 430 through a vent 440. This chamber 430 is isolated from the remainder of the circuitry by a barrier 445. The opposite end of the device 400 has a micro USB port 450 for charging the device.

As shown in the exploded view of FIG. 6B, the PCB 460 is secured to the base 415 of the housing using screws 462a-d through holes 465a-d into depressions/screw receivers 442a-d, and the base 415 is secured to the main housing 410 using screws 464a-b through holes 444a-b. The opposite end of the base 415 (towards the opening 420) may be inserted into a slot (not shown) in the main housing 410 prior to securing the base 415 to the main housing 410 with the screws 464a-b.

Figure 4:
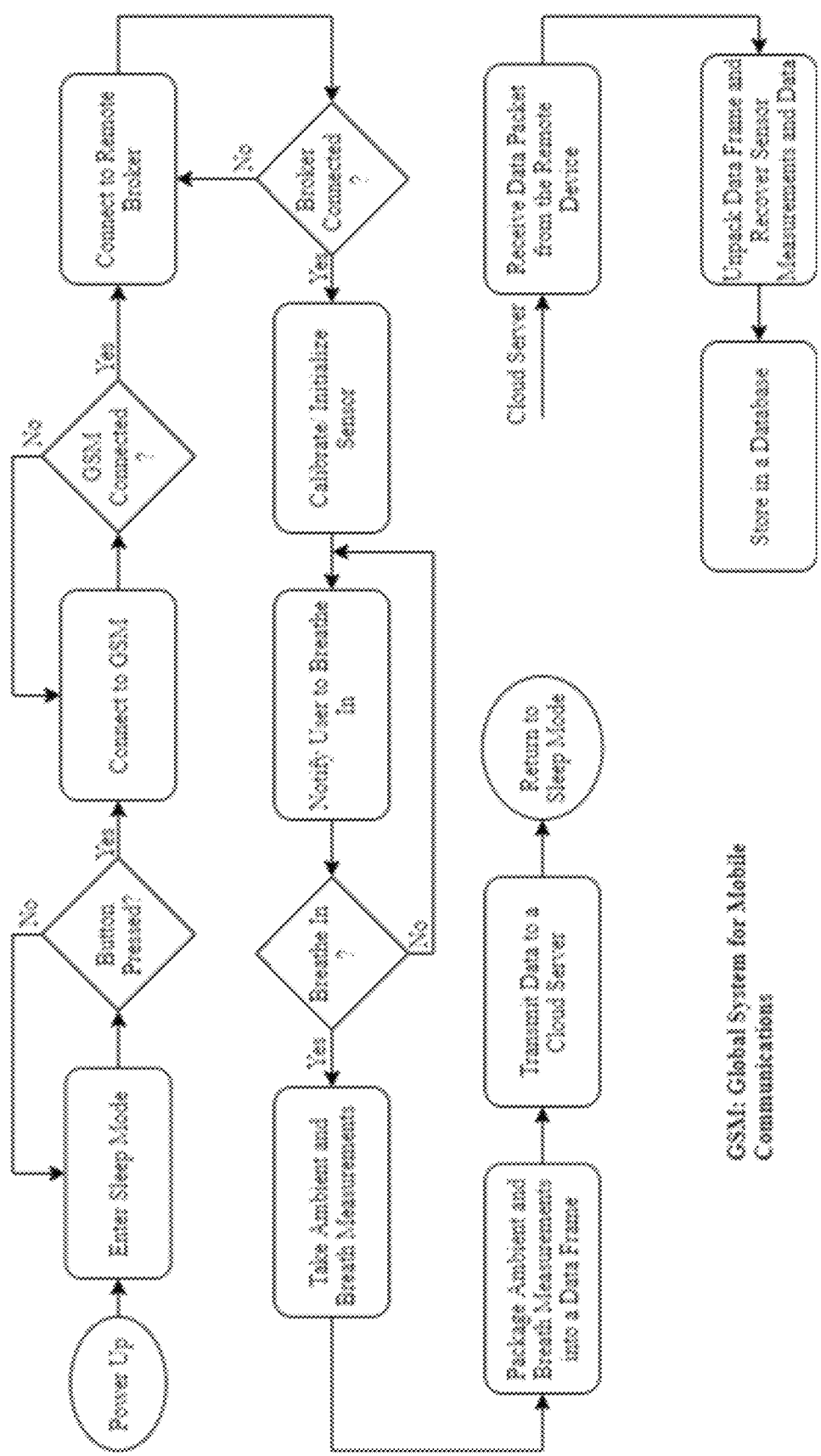
FIG. 4 is a flow chart for an exemplary method of using the present device to collect breath data from a patient and transmit, classify and store the data in a cloud-based data storage service.

An exemplary flow chart for a method of use of the device 300 is shown in FIG. 4. A test is initiated by pressing the "Start" button ("Button Pressed?" in FIG. 4). This initiates a series of events, including establishing GSM and message queuing telemetry transport (MQTT; the "Broker" in FIG. 4) connections and sensor initialization (warm-up and calibration). In one example, the events following "Start" button-based initiation take about four minutes. "Device ready" status is indicated by blinking the LED and/or displaying a green color ("Notify User to Breathe in" in FIG. 4), upon which the user takes a deep breath and slowly breathes into the sensor. In one example, the user exhales into the device three times, but other numbers of exhalations are acceptable. The breath enters the sensors 270 and escapes through the perforated openings 120 in the upper housing section 100/310. When breath flow is detected (e.g., by a sudden temperature change and/or a VOC sensor change), sensor readings are recorded. These steps are programmable and can be modified to meet specific patient and/or study needs.

For example, just before the patient exhales into the device 300, a plurality of ambient samples are taken (e.g., 3-20, and in one example 10 ambient samples) are taken. When the device is ready, the patient's breath is sampled at a predetermined rate (e.g., 1-10 samples/sec) during the period of time for which the patient is expected to exhale (e.g., 5-15 sec). Breath sampling may be repeated one or more times (e.g., 1-4 times). In one example, the sampling rate is 2 samples/sec, the patient exhalation period is 10 sec, and the breath sampling is repeated twice, for a total of 60 samples per test. The recorded sensor readings (which may be pre-processed by the MCU) are then packaged (e.g., organized into a frame or packet) for wireless transmission to a cloud-based data storage service, such as Amazon Web Services (AWS). Preprocessing may include filtering, averaging, identification of high and/or low values, determining a mean value and/or standard deviation, etc. Raw and/or summary sample information may be packaged and transmitted.

A device ID unique to the device 300 and the sensor readings (e.g., including the samples of the ambient environment prior to breath sampling) are packaged and sent to the cloud (e.g., using the MQTT protocol). Timestamps may be obtained using a network time protocol (NTP). The received data is parsed and written into a database (e.g., DynamoDB, available through Amazon Inc. at https://aws.amazon.com/dynamodb). The device 300 may indicate reading, sampling and/or transmission success by displaying a different color or pattern (e.g., an orange color, flashing a single color at a different rate or alternating between multiple colors [e.g., a "rainbow" color or display]) on the LED 250, then it may enter a sleep mode to conserve the battery 210. If the data transmission fails after one or more attempts, the data may be saved (e.g., in an on-board memory, on the PCB 130 or in the MCU), and transmission can be retried later. No additional action is necessary from the user. For example, the device 300 can wake up after a predefined time (e.g., 1-60 minutes), retry the transmission, and go back to sleep without alerting the user. These steps can be modified to meet specific patient and/or study needs.

The MCU on the device 300 can run trained machine learning algorithms. A trained model (e.g., a machine learning algorithm trained to detect and/or analyze patterns in the sampled data) can be directly loaded on the device 300 without any hardware modifications. For example, commercially available sensors have been tested with VOC biomarkers of diabetes at concentration levels found in diabetes patients' breath, using simulated breaths representing low and high BG levels. The data on the simulated breaths were used to train an available/downloadable support vector machine (SVM). For example, MATLAB, the Classification Learner supervised machine learning app (available from Mathworks, Inc. at https://www.mathworks.com/help/stats/classificationlearner-app.html) allows quick comparison of supervised machine learning using various classifiers. Alternatively, the scikit-learn predictive data analysis tool (available from Python.org at https://scikit-learn.org) can be used to conduct the machine learning and generate the trained software model/algorithm. Next, the trained model was implemented in a microcontroller and tested with simulated breaths in real-time. The handheld breathalyzer-type sensor device 300 in FIGS. 5A-B was then made with the microcontroller and other capabilities to record sensor data and wirelessly save the data on the cloud incorporated therein.

Studies of VOC biomarkers of diabetes in human breath have been conducted by the present inventor and others, including correlation of VOCs in diabetes patients' breath with blood glucose level or state. For studies supporting the present invention, acetone and ethanol were used as the VOC biomarkers. Concentrations of acetone and ethanol corresponding to low (≤100 mg/dL) and high (≥125 mg/dL) BG are shown in Table 1 below.

TABLE 1

VOC biomarkers and corresponding concentrations of low and high BG groups.

| Compound | Low BG Level (<100 mg/dL) | High BG Level (>125 mg/dL) |
| --- | --- | --- |
| Acetone | 1-3 ppm | 5-7 ppm |
| Methyl Nitrate | 1 ppm | 3 ppm |
| Ethanol | 0-20 ppb | 35-50 ppb |
| Methanol | 0 ppb | 1 ppb | ppm: Parts-per-million,
ppb: Parts-per-billion

Sensors that detected the selected VOCs (acetone and ethanol) at the concentration levels indicated in Table 1, but with varying selectivity and sensitivity, were obtained from Figaro Inc. Acetone and ethanol were used to characterize new sensors for sensitivity, warm-up time, rise and fall times, stability, and degradation. Four metal oxide semiconductor (MOS) VOC sensors used for testing and training the SVM, the corresponding VOCs tested by the manufacturer, and the smallest concentration that the manufacturer considers to be reliably detectable are shown in Table 2 below.

TABLE 2

Four commercially available metal-oxide semiconductor based VOC sensors, compounds tested by the manufacturer, and the smallest concentration tested.

| Sensor Part No. | Manufacturer Tested Compounds | Smallest Conc. Manufacturer Tested |
| --- | --- | --- |
| TGS2600 | $H_2$, Ethanol, Iso-butane, Methane | 1 ppm |
| TGS2602 | Toluene, Ethanol, Ammonia, $H_2$, $H_2S$ | 0.1 ppm |
| TGS2603 | Ethanol, TrimethylAmine, Methyl Mercaptan, $H_2$ | 0.1 ppm |
| TGS2620 | Ethanol, Hydrogen, Iso-butane, CO, Methane | 50 ppm |

Figure 7A:
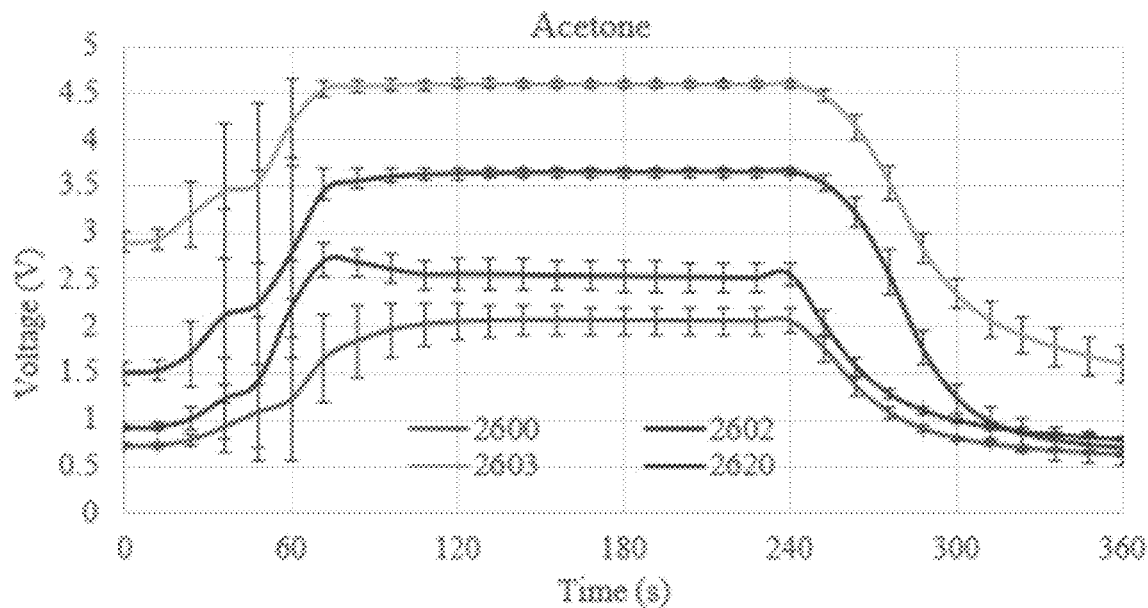
FIGS. 7A-B are graphs showing responses over time of exemplary sensors to certain VOCs in model samples of diabetes patient breath in testing in support of the present invention.
Figure 7B:
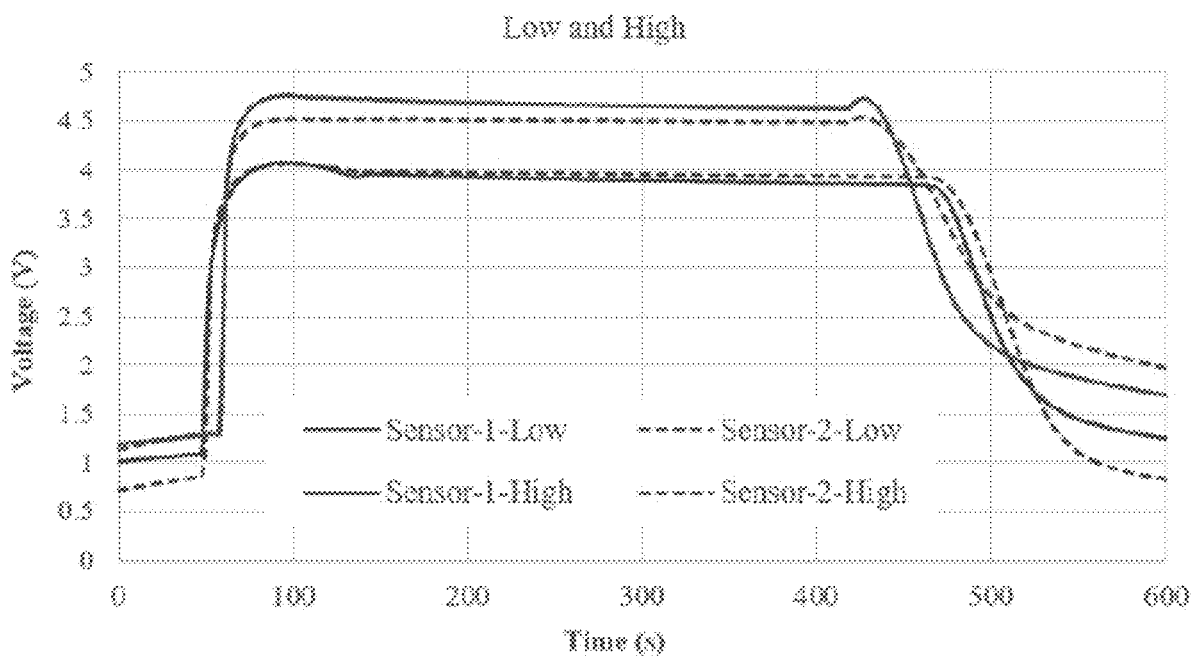

In tests supporting the present invention, the sensors detected acetone and ethanol at part per billion (ppb) levels. FIG. 7A shows the responses of the four sensors to acetone in the tests. FIG. 7B shows results/data from the sensors TGS2600 ("Sensor-1") and TGS2602 ("Sensor-2") with humidified air spiked with acetone and ethanol, at concentrations corresponding to low and high BG levels as shown in Table 1 above.

Simulated human breath was made in a series of chambers and tested with the above-described sensors to obtain the data shown in FIGS. 7A-B. Ultra-pure air (80% nitrogen and 20% oxygen) was used as the carrier. The air was percolated through deionized water to introduce humidity to simulate the humidity of exhaled breath. The humidified air entered a chamber containing the VOC. In this chamber, an amount of VOC vapor representing a low BG level or a high BG level was introduced using a micro needle. The amount of VOC was determined based on its desired concentration, the molecular weight of the VOC, and the volume of the chamber. The evaporated VOC was transported to the next chamber containing a sensor array (the Sensor Chamber). The evaporated VOC in the humidified carrier was transported at a flow rate of 0.5 L/min for 45 seconds from the VOC Chamber to the Sensor Chamber. Results for two sensors in response to simulated breath containing acetone and ethanol concentrations corresponding to low and high BG levels are shown in in FIG. 7B. Data from repeated experiments with slight variations in the VOC concentrations were collected over several weeks and used for training and testing a support vector machine (e.g., as described herein). The steady-state portion of the sensor response was used in a cross-validation method to determine the SVM parameters. The trained model was then implemented on a microcontroller (e.g., an ATMega-based microcontroller) to create an embedded SVM, and the embedded SVM was tested in real-time using simulated breath (i.e., the humidified carrier) containing the VOC at a concentration corresponding to a low or high BG level. The trained embedded SVM model classified simulated breath with 97.1% accuracy. Using the results from the above studies, a hand-held device with a breathalyzer-like design and an ability to automatically log data on the cloud (e.g., device 300 in FIGS. 5A-B) was developed.

Even though breath VOC biomarkers of diabetes have been known for some time, a breath-based BG monitoring solution does not (to the best of the inventor's knowledge) currently exist. Past efforts have not come to fruition because of two significant challenges. First, the failure of research-stage sensors to consistently produce reliable readings outside of the lab. Second, because of the nature and quantity of the test data collected in the past, the prediction models did not work reliably when tested in real-life situations. The present invention overcomes those barriers by collecting data in real-life situations using commercially available sensors and applying relatively rigorous testing and analysis to generate a reliable trained machine learning model.

To improve the reliability of the SVM training, a number of patients (e.g., 10-1000, and in one example, 50) with type-2 diabetes can take the present sensor device to their home and collect test data over a predetermined period of time (e.g., 7-365 days, and in one example, for twelve weeks). Patients can blow into the sensor a predetermined number of times (e.g., 1-4, and in one example, twice) a day using a deep breath, optionally repeating the sensor test a number of times (e.g., 1-3 times). The sensor tests should be taken soon after the prescribed finger-stick BG measurements (e.g., within 1 hour). The patients record the date, the time, the finger-stick BG measurement, and optionally, other notes such as eating schedule (e.g., fasting, after meal), exercise schedule, etc., preferably on a supplied BG tracking chart. Each patient may thus perform 7-1460 tests, or any number or range of numbers therein (in one example, 168 tests). This may generate 70-1,460,000 tests total from all of the patients, although a total number in the range of 1000-15,000 tests should suffice. Each test can provide 20-600 (or more) data points (in one example, 210 data points, including ambient samples and breath samples). Such a data set is large enough for training and validation of the machine learning model, with a high accuracy. For example, in the above study using simulated breath and two MOS sensors, an SVM trained with data from 20 tests, each test containing 250 samples/data points, correctly classified 731 out of 753 new tests on simulated breath samples (97.1% accuracy).

The device 300 has been tested for collecting samples of a user's breath and transmitting data from the samples, specifically data from sensors 270 for one or more VOCs associated with type-2 diabetes patients. The device 300 can also be used to collect and transmit large-scale breath data from patients in real-life situations, to analyze other diseases such as lung cancer, breast cancer, heart disease, stress, colorectal and prostate cancers, asthma, and other diseases. The device 300 can also be used in other applications, such as environmental data collection, indoor air data collection, and structure monitoring.

Figure 8:
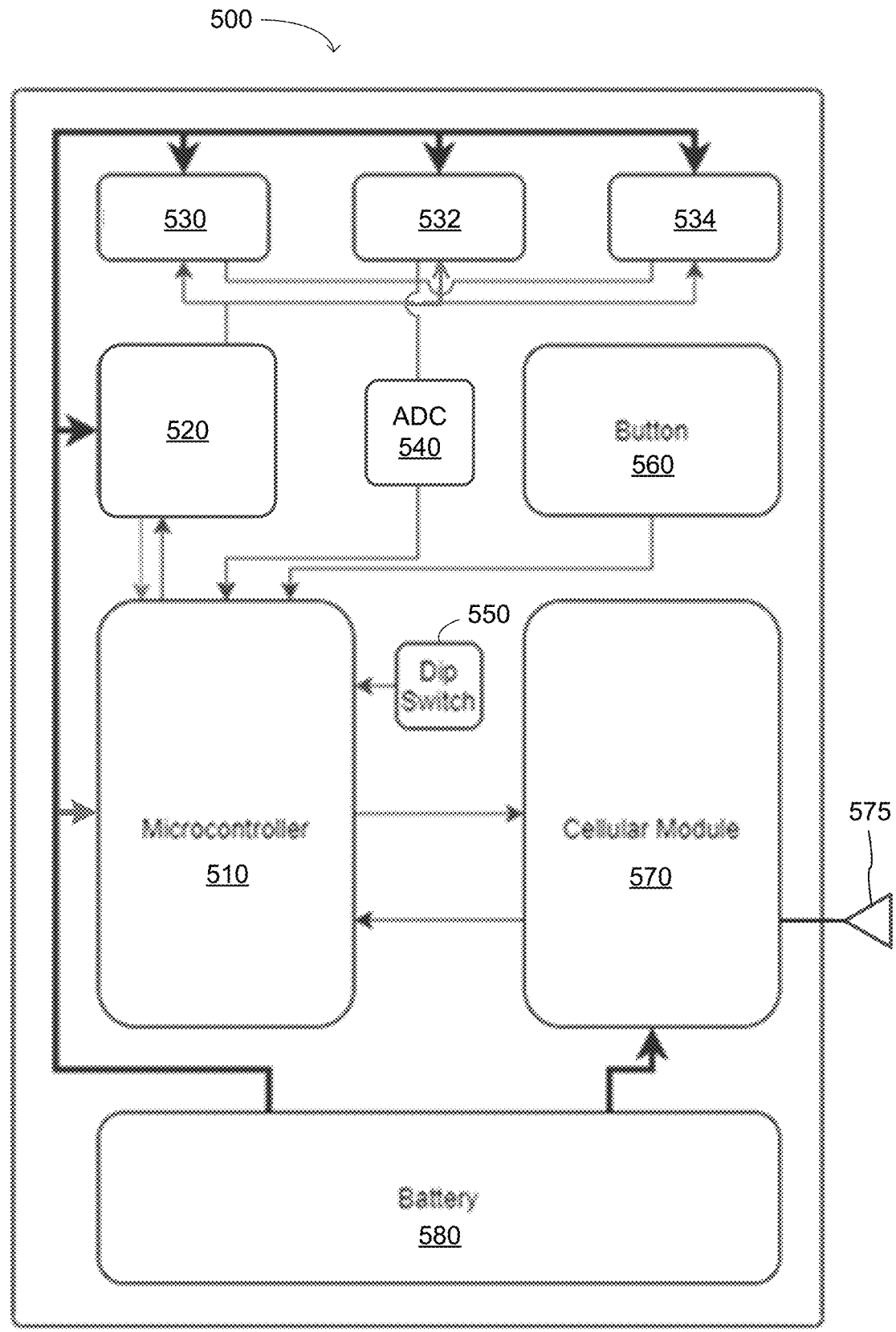
FIG. 8 is a block diagram of another exemplary circuit board suitable for use in the present device.

FIG. 8 shows a block diagram of another exemplary circuit board 500 suitable for use in the present device. The circuit board 500 has an architecture that enables rapid, facile calibration. The circuit board 500 includes a microcontroller 510, a digital potentiometer (or digital potentiometer array) 520, a plurality of sensors 530-534, an analog-to-digital converter (ADC) 540, a dual in-line package (DIP) switch 550, an on/off button 560, a cellular module 570, an antenna 575, and a battery 580. The microcontroller 510 may be as described in other embodiments, but in one example, is a conventional, commercially available 32-bit microcontroller (e.g., from ST Microelectronics, Scottsdale, Arizona), running an ARM® processor (available from Advanced RISC Machines, Cambridge, England), and having low power consumption and the capability to implement machine learning algorithms, but other bit sizes (e.g., 8, 16, 24, 64, etc.) and other processors and architectures (e.g., 8051, PIC [developed by Microchip Technology, Chandler, Arizona], MIPS, MSP [developed by Texas Instruments, Dallas, Texas], Harvard architecture, etc.) that are able to implement machine learning algorithms may also be used.

The digital potentiometer 520 may have a width of 4 to 16 bits, but is a 10-bit digital potentiometer in one example. An algorithm run by the microcontroller 510 that controls the digital potentiometer(s) maintains an optimal operating resistance for each of the sensors 530-534. Specifically, the operating resistance is controlled so that the sensor(s) can be read by the microcontroller 510 within the operating range of the ADC 540. An example of a commercially available digital potentiometer 520 is the MCP41/423X family of potentiometers from Microchip Technology (Chandler, Arizona).

The sensors 530, 532 and 534 are as described herein, but in the example of FIG. 8 shown, comprise an alcohol and/or organic solvent vapor sensor, a volatile organic compound and/or odorous gas (e.g., $NH_3$, $H_2S$) sensor, and a gas-phase hydrocarbon (e.g., methane, propane, butane) sensor. The sensors 530-534 may be in a transistor outline (TO) package, to facilitate placement and mounting on the circuit board 500. Examples of suitable sensors include the TGS 2602, TGS 2612, and TGS 2620 sensors from Figaro Inc. (Osaka, Japan).

The ADC 540 may also have a width of 4 to 16 bits, similar to the digital potentiometer 520, and is a 10-bit ADC in one example. Thus, the width of the ADC 540 may be equal to that of the digital potentiometer 520, but this is not a requirement. Advantageously, when the ADC 540 has a width of 8 bits or less, the width of the digital potentiometer 520 is within two bits of the width of the ADC 540, and when the ADC 540 has a width of more than 8 bits, the width of the digital potentiometer 520 is an integer within 25% of the width of the ADC 540. In some embodiments, there is one ADC for each sensor 530, 532 and 534. The ADC 540 is conventional and commercially available. In various examples, the ADC 540 can be an AD9410 ADC from Analog Devices, Inc. (Norwood, Massachusetts), a TLC155x ADC from Texas Instruments (Dallas, Texas), a MAX1204 ADC from Maxim Integrated (San Jose, California), a MCP300x ADC from Microchip Technology (Chandler, Arizona), etc.

Figure 9A:
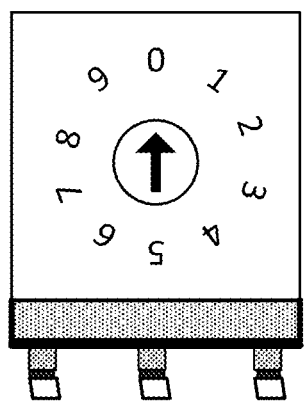
FIGS. 9A-C show examples of devices suitable for use in the exemplary circuit board of FIG. 8.
Figure 9B:
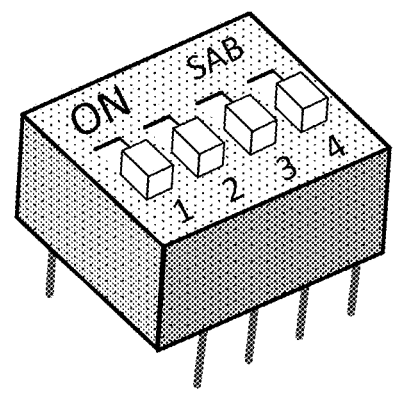

The DIP switch 550, examples of which are shown in FIGS. 9A and 9B, may define the duration of the sensor heat-up period. Each separate/independent setting on the DIP switch 550 may specify a different length of time for heating up the sensor, which may be from 10 seconds to 30 minutes, although the invention is not limited to this range. The DIP switch 550 may have a width of from 3 to 8 bits, and in one example, is a 4-bit switch.

The button 560 is a conventional on/off button, as described herein. Alternatively, the button 560 can be replaced with a conventional on/off switch, but a button is generally more convenient for use in a relatively small handheld device.

The cellular communication module 570 is conventional, and is operably connected to the antenna 575 to communicate wirelessly with an external computer, workstation, server, notepad computer, etc., for further processing and/or improved visualization of the data. The cellular communication module 570 may comply with various data communication standards and protocols, such as LTE, WiMAX, WLAN (e.g., Wi-Fi), WAN, W-CDMA, Bluetooth, ZigBee, NFC, LoRaWAN, etc. Alternatively, the cellular communication module 570 may comprise an integrated circuit having the ability to transmit and receive wireless data signals using such standard data communication protocols. Generally, the cellular communication module 570 comprises a 8- to 32-bit processor, 256 kB-8 MB of flash memory, 64 kB-2 MB of random access memory (RAM), 4-40 mixed signal general purpose input/output (GPIO) ports configured to communicate using various conventional protocols (e.g., UART, I2C, SPI, etc.), a cryptographic and/or security block or module (built-in or added on), a cellular network coprocessor, and a cellular modem, and a transmitter capable of (wireless) signal transmission at a power of from −24 dBm to +10 dBm (or any range of values therein, such as −20 dBm to +8 dBm). In some examples, the cellular communication module 570 may comprise a separate board, mounted on or operably connected to the circuit board 500.

Figure 9C:
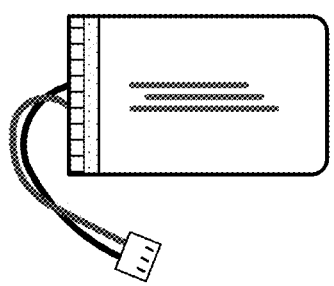

The battery 580 is a conventional rechargeable lithium ion battery, although other rechargeable batteries that can provide sufficient power to the components on the board 500 are also acceptable. In some embodiments, the battery 580 is a pouch-type Li polymer battery, providing 500-2000 mAh of power at a maximum voltage of 3.0-5.0 V. FIG. 9C shows an example of a battery that is suitable for use in the present device. Such batteries are commercially available from Shenzhen Data Power Technology Ltd. (Shenzhen, China), and many other manufacturers.

In some embodiments, the circuit board 500 may automatically calibrate the sensors 530-534. In one example, the sensors 530-534 were each heated separately for four (4) minutes during a calibration test. While the sensor was heating, an analog voltage is read from the sensor and compared to a selected target value. For example, for a 10-bit ADC 540, the target value was 256. Depending on the difference between the analog voltage reading and the target value, the digital potentiometer adjusts its resistance accordingly to position the analog voltage value read from the sensor as close to the target value as possible. This process repeated each second for the duration of the sensor heating time.

Figure 10A:
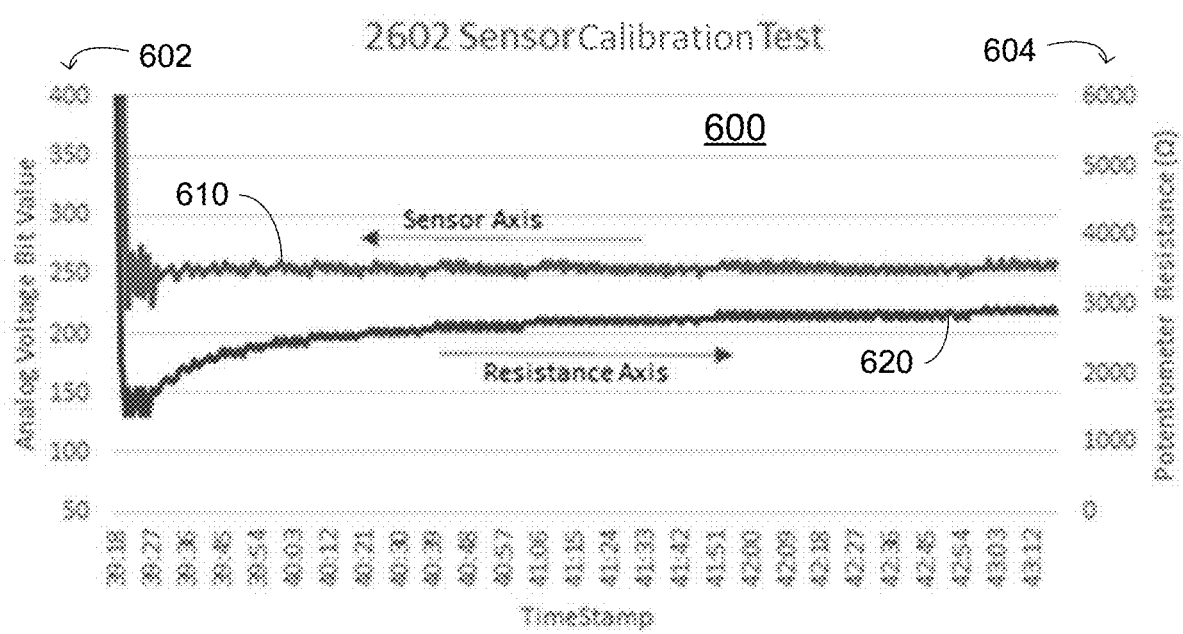
FIGS. 10A-D are graphs of the results of calibration tests of certain sensors useful in the present device.
Figure 10B:
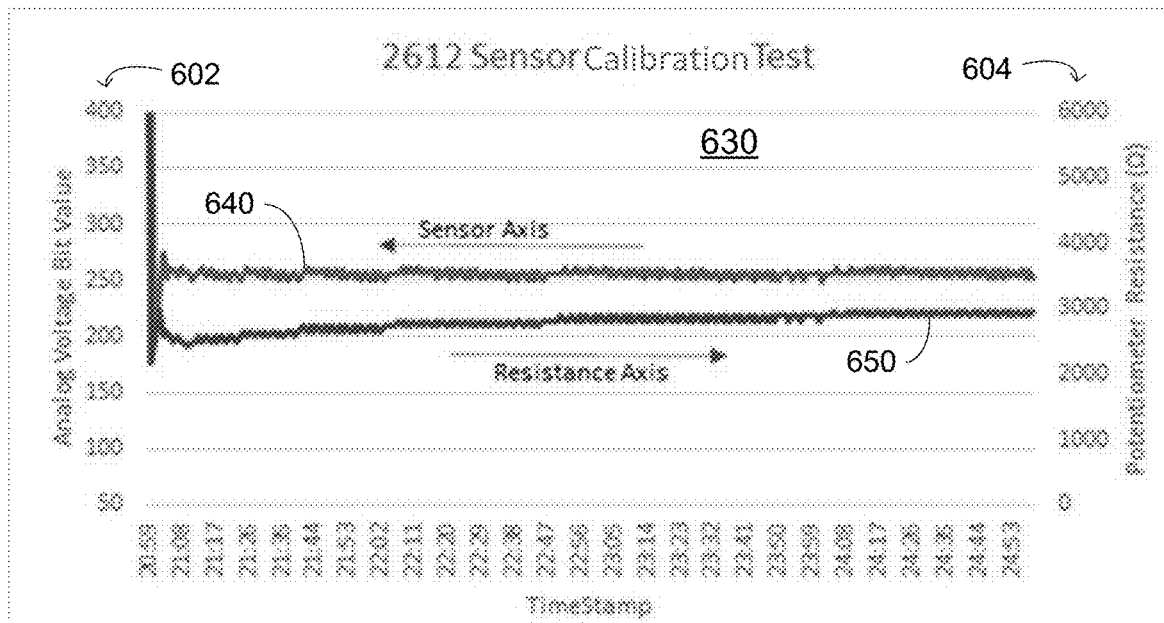
Figure 10C:
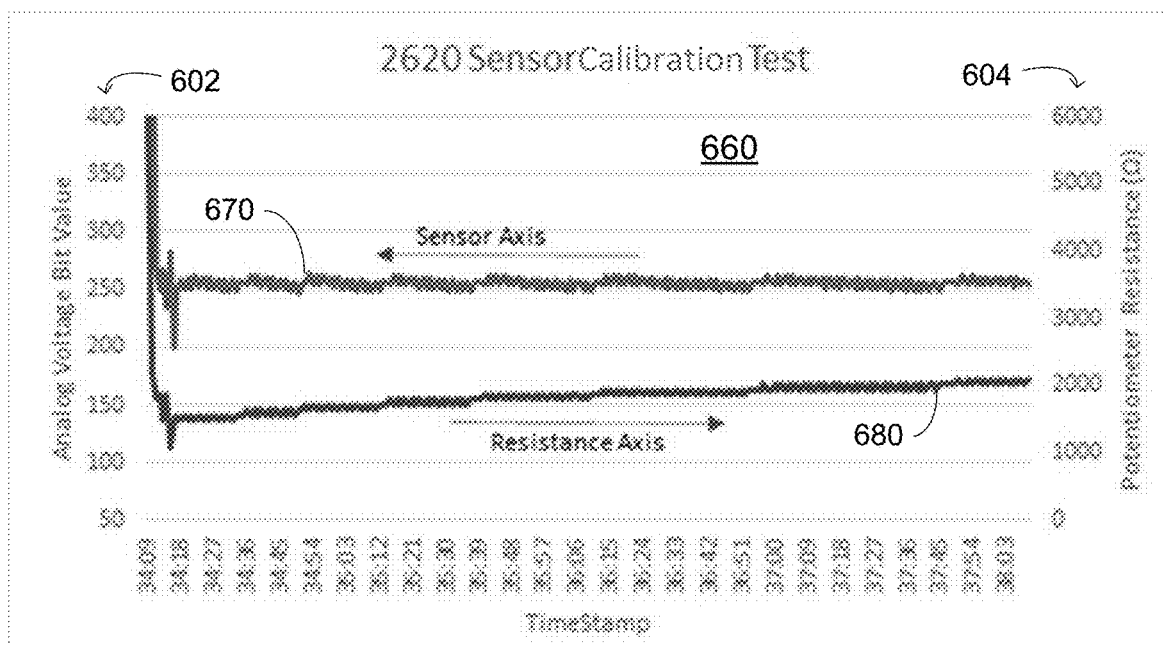

FIGS. 10A-C show results for an automatic calibration test with three sensors (TGS 2602, TGS 2612, and TGS 2620, obtained from Figaro Inc., Arlington Heights, Illinois). In each case, one sensor at a time was connected to an external voltage divider circuit (i.e., not on the circuit board 500) through an MCP4131 digital potentiometer. The calibration algorithm in the microcontroller starts the potentiometer at an arbitrary resistance value, and adjusts the resistance output by the potentiometer to move the analog voltage from the sensor to value corresponding to the target ADC value (256). As seen in FIGS. 10A-C, the algorithm quickly adjusts the potentiometer resistance towards a value that moves the sensor voltage towards the target ADC value, and maintains the potentiometer resistance near the value at which the sensor voltage matches the target ADC value. In the tests shown in FIGS. 10A-C, the algorithm along with the potentiometer moved and maintained the sensor voltage within 5% of the target ADC value over the course of the four-minute test window.

The graphs 600, 630 and 660 in FIGS. 10A-C display the ADC bit value corresponding to the analog voltage from the sensor (lines 610, 640 and 670) and the calculated digital potentiometer resistance (lines 620, 650 and 680). The left axis 602 shows the analog voltage value read from the sensor (as a bit value of the ADC), and the right axis 604 represents the resistance for the potentiometer. The tests were conducted (and subsequent measurements taken) over the course of multiple hours, but the graphs 600, 630 and 660 display only the first four-minute period. The data/results during the tests not shown in the graphs 600, 630 and 660 are consistent with the trends shown in the graphs 600, 630 and 660.

Figure 10D:
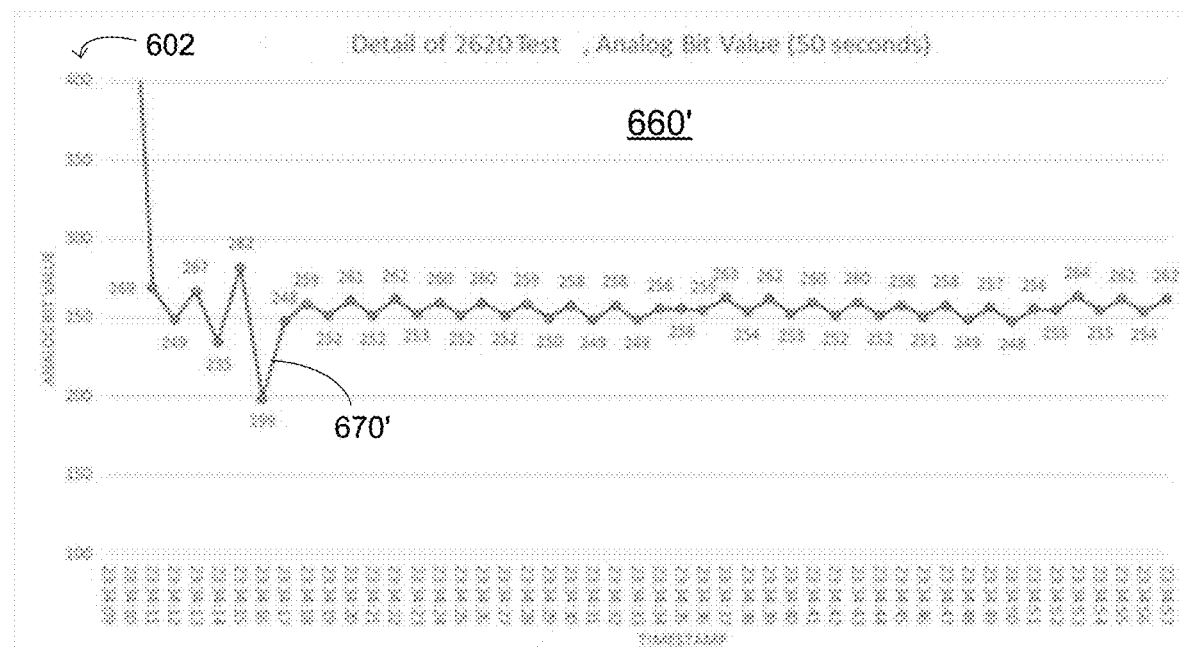

As is shown in FIG. 10D, during the first few seconds of the test, the analog sensor voltage changes rapidly. After this initial period of relatively high variability and/or fluctuation, the sensor voltage (line 670') is maintained near the target value (256; the numbers above/below the data points on the line 670' are the values corresponding to the measured sensor voltage), while over time, the potentiometer's resistance (lines 620, 650 and 680 in FIGS. 10A-C) rises to compensate for the gradual changes of the sensor as it heats up during the test. As each sensor heats up, its resistance increases slowly, at a rate that is dependent on the environmental conditions of the test.

Figure 11:
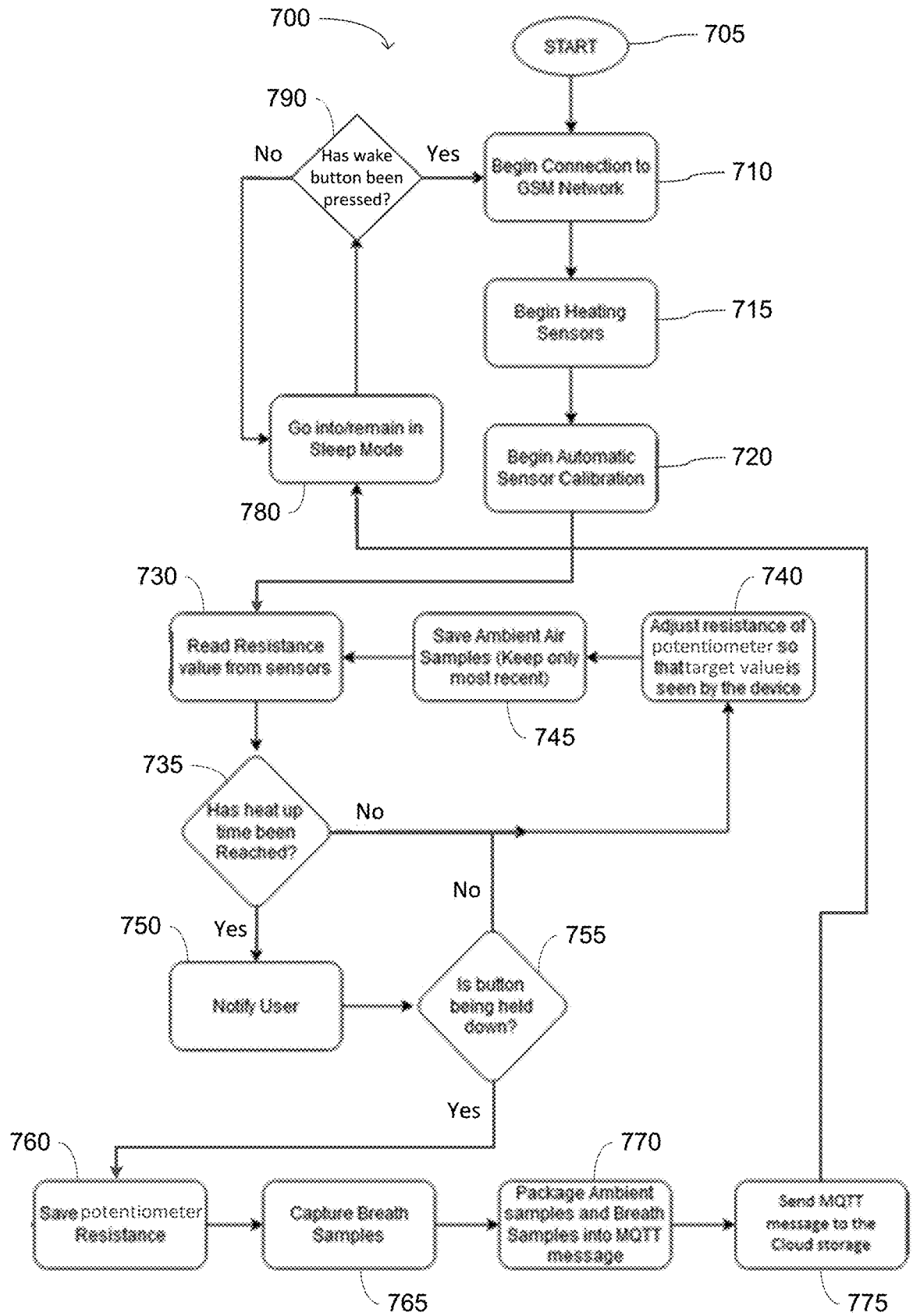
FIG. 11 is a flow chart for an exemplary method of calibrating and using a device comprising the exemplary circuit board of FIG. 8.

FIG. 11 shows a flow chart for a method 700 of automatically calibrating, then using, the present device to sample a person's breath for the presence and/or concentration of certain volatile organic (and optionally inorganic) molecules, such as acetone, ethanol, methanol, methyl nitrate, isoprene, propane, benzene, ethyl benzene and carbon monoxide. The presence and/or concentration of certain volatile organic compounds (VOCs) correlate to a patient's known blood glucose levels (e.g., sampled by direct testing of the patient's blood) to form a "VOC signature" of the patient's blood glucose level as determined by (and correlated to) the VOCs in the patient's breath, which the sensors in the present device sample and report to the device user, such as the patient or a medical professional (as described herein).

The method 700 starts at 705 by turning on the device, which connects to a data communication (e.g., GSM) network at 710. At the same time, the device begins heating the sensors at 715. As soon as possible thereafter, the device automatically begins calibrating the sensors at 720.

Thereafter, at 730, the device reads (e.g., samples) the resistance values from the sensors. Alternatively, at 730, the device may read (e.g., determine) and optionally report analog voltage values from the sensors. Regardless of the parametric value being read from the sensors, the device may read the parametric value from the sensors periodically (e.g., once every second, once every 10 seconds, or any time period or frequency therebetween), until the end of a predetermined time period for heating or warming up the sensors ends. This predetermined heating or warming time period may be from 10 seconds to 10 minutes, or any time length of range of time lengths therein.

Until the end of the predetermined sensor heating or warming time period (i.e., "No" at 735), the method automatically adjusts the resistance of the potentiometer (or other series resistor-based voltage divider) at 740 every time that the parametric value is read from the sensors to bring the parametric value(s) closer to the target value. As explained above, when using a 10-bit ADC, the target value may be a voltage corresponding to a bit value of 256, but other values (e.g., between 128 and 512) are also suitable. In general, when the target value is a voltage corresponding to an ADC bit value, the target value may be from 0.1 to 0.5 times the number of ADC states (i.e., $2^x$, where x is the bit width of the ADC). Alternatively, when the target value is an actual voltage, the target value may be from 0.1 to 0.5 times the theoretical maximum output voltage of the sensor. At 745, the data samples (which are effectively the VOCs sampled in the air in the device) are saved, either on the device itself, in a computer or other data processing terminal communicatively connected to the device, or both. In some embodiments, only the most recent data sample is saved. The loop 730-(735)-740-745 repeats itself until the end of the predetermined sensor heating or warming time period.

When the predetermined sensor heating or warming time period expires ("Yes" at 735), the user is notified at 750 that the sensors have been calibrated and/or that the device is ready for use to test/sample the patient's breath. At this point, if the button on the device is pressed down by the user or patient at 755, the method 700 moves to a phase in which the patient exhales into the device and the patient's breath is sampled by the sensor(s). However, if the button is not pressed down at 755 (e.g., within 1-10 seconds of notification after the expiration of the sensor heat-up or warm-up time period), the method 700 returns to 740 and continues calibrating until the user or patient presses the button on the device within a set amount of time after notification at 755.

When the button on the device is pressed down at 755, the device saves the potentiometer resistance value at 760, and the patient exhales into the device as described herein. In various embodiments, the patient may exhale 2-5 times into the device over the course of 1-5 minutes, although the invention is not limited to these values. The device captures the sensor data from the patient breath samples at 765, then all of the sensor data (at least the final calibration reading and all of the sensor data collected from the patient breath samples) is packaged for wireless transmission, optionally along with time stamps for each data sample. In one embodiment, the sensor data is packaged into a message queuing telemetry transport (MQ Telemetry Transport, or MQTT) packet or message, but other data packaging protocols and standards are acceptable. The sensor data packet or message format may comprise a header (e.g., having a length of 1-4 bytes and/or containing control, formatting and/or packet/message length information) and a payload containing the sensor (and optionally, the time stamp) data. The sensor data packet or message may have a minimum size/length (e.g., 2 bytes) and a maximum size/length (e.g., 256 MB, but greater or different maximum lengths may be possible in other formats or standards).

At 775, in one embodiment, the packet or message containing the sensor data is transmitted to a cloud-based data storage system. Alternatively, the packet or message containing the sensor data may be transmitted to the computer or other data processing terminal communicatively connected to the device. After transmitting the packet or message, the device may experience a period of inactivity. After a predetermined time of inactivity (e.g., from 15 seconds to 2 minutes, or any time length or range of time lengths therein, although the invention is not limited to these time lengths), the device may go into a sleep mode at 780, in which the device powers down many components therein, such as the sensor heaters, the potentiometer, the ADC, the switch, the microcontroller, and optionally, the communication module. The device remains in the sleep mode until the wake button (e.g., the button 560 in FIG. 8) is pressed at 790, at which point the method 700 returns to 710 to reconnect the device to the data communications network.

Figure 12:
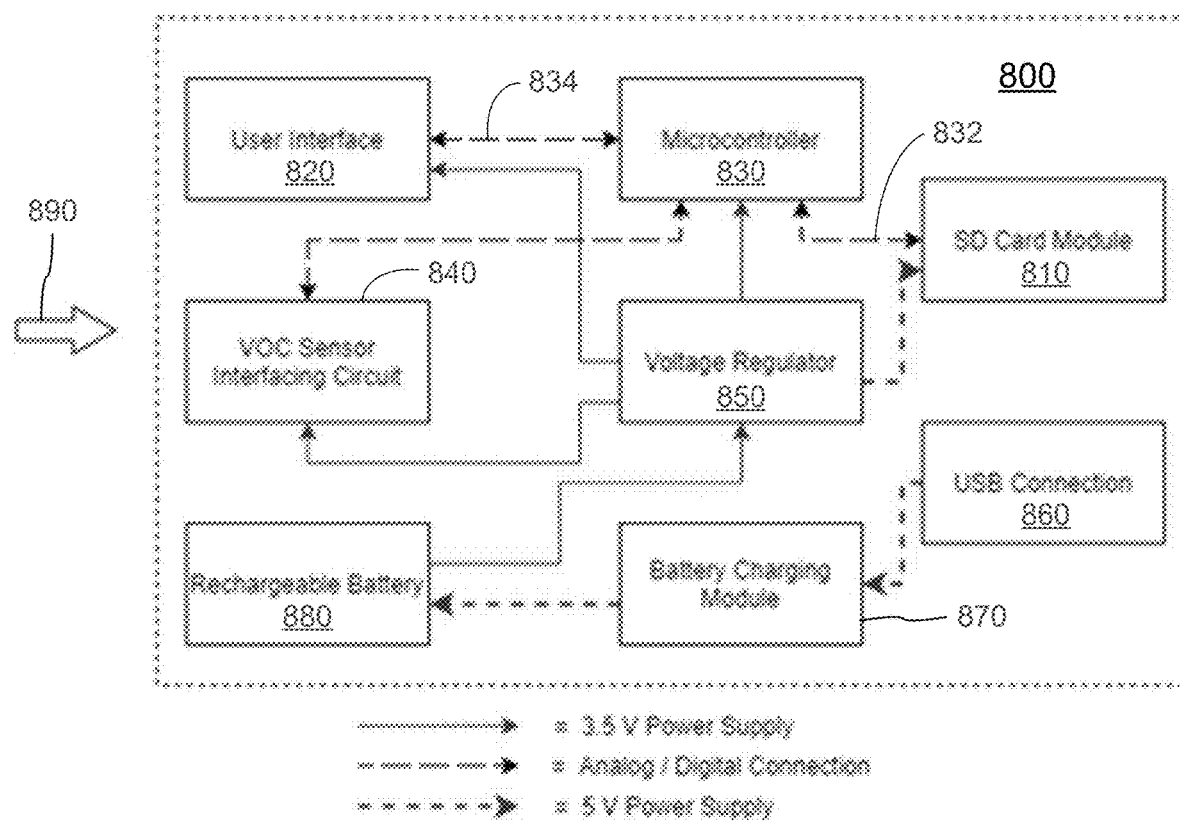
FIG. 12 is a block diagram of yet another exemplary circuit board suitable for use in the present device.

FIG. 12 shows a block diagram of another embodiment of a circuit board 800 useful in the present device that includes a memory card module 810 (e.g., a secure digital [SD] card module, a secure digital high capacity [SDHC] card, a secure digital extended capacity [SDXC] card, etc.) and a display or user interface 820. Other types of memory cards and memories, such as compact flash memory cards, flash memory modules, random access memory modules, or even a USB flash drive or thumb drive may be useful in the present device 800. The display or user interface 820, an example of which is shown in FIGS. 13 and 14A-F, may comprise a liquid crystal display, an electrochromic display, a light-emitting diode (LED) display, or a conventional touchscreen.

Each of the memory card module 810 and the display or user interface 820 communicates with the microcontroller 830 (which is as described herein) through an analog-to-digital converter (ADC). In other words, the memory card module 810 and the display or user interface 820 respectively send analog signals on two-way buses 832 and 834, and an ADC (not shown) converts the analog signals to digital signals for reception by the microcontroller 830. Likewise, the microcontroller 830 sends digital signals on buses 832 and 834, and a digital-to-analog converter (DAC; also not shown) may convert some of the digital signals to analog signals for reception by the memory card module 810 and the display or user interface 820.

The memory card 810 provides (i) local data storage for the microcontroller 830 to retrieve data directly from the device 800 and (ii) a backup storage device for sensor data in the event the cellular connection (e.g., through cellular module 570 [FIG. 8], which is also connected to the microcontroller 830 in substantially the same manner as in FIG. 8) fails. The display or user interface 820 provides a mechanism for interaction with the user (e.g., for displaying information to and receiving input from the user).

Figure 13:
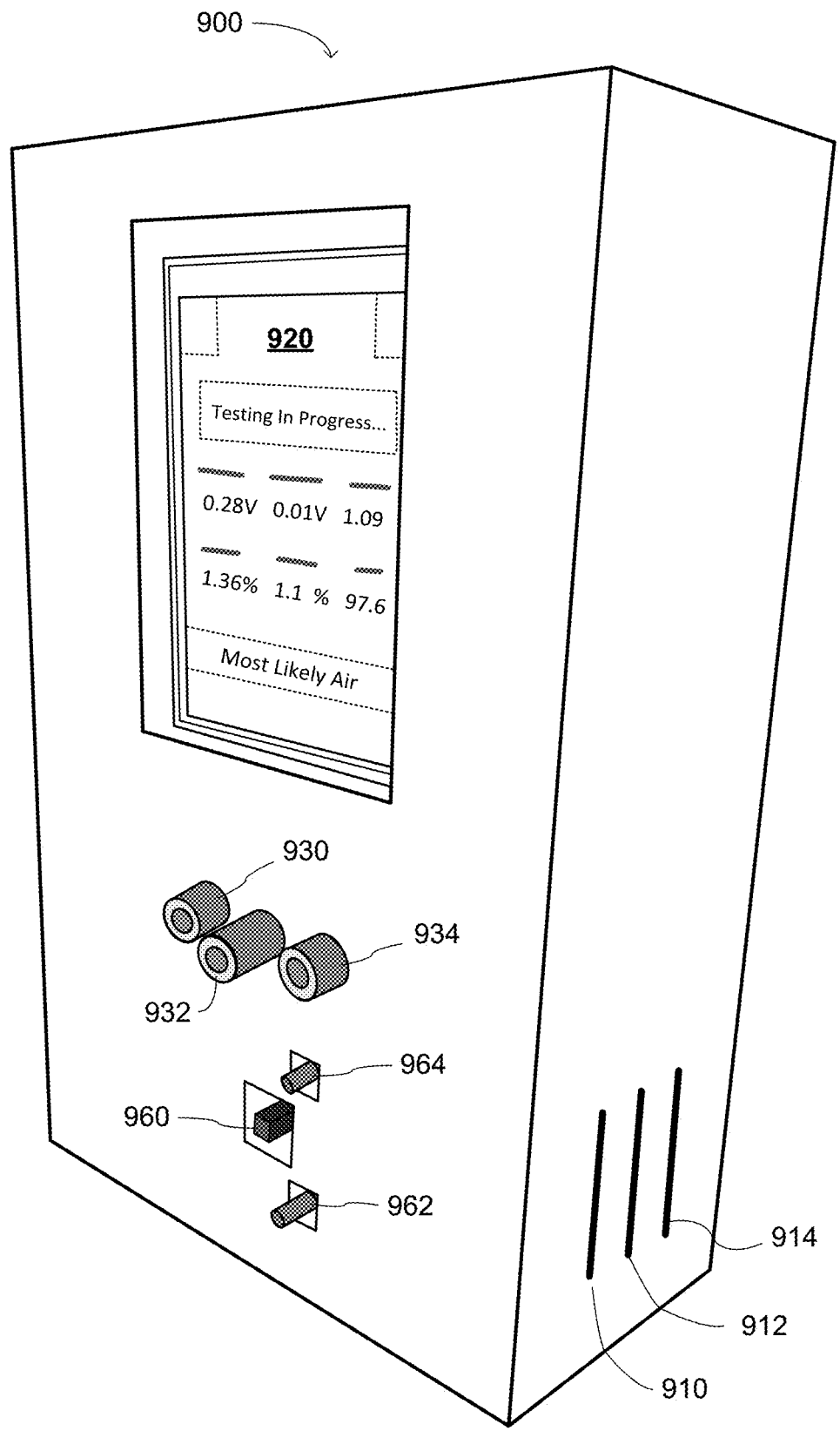
FIG. 13 depicts an exemplary prototype device with a display/user interface in accordance with embodiments of the present invention.

An exemplary user interface containing a display 920 is shown in the prototype device 900 in FIG. 13. The display 920 comprises a 2.8-in (7.1-cm) thin film transistor (TFT) LCD that communicates with the microcontroller 830 over a serial peripheral interface (SPI). The user interface in the prototype device 900 may also comprise a digital pad or D-pad (not shown, but similar to those in many handheld digital video games) and push buttons 960, 962 and 964. The button 960 may be an on/off button, similar to the button 560 in FIG. 8. Alternatively, the digital pad may be integrated into the housing of the device 900, or replaced with a joy stick and a selection button, and the display 920 and optionally one or both of the push buttons 962 and 964 may be replaced with a touch screen. The slots 910, 912 and 914 in the prototype device 900 may be vents for air flow/cooling, or openings for electrical connectors, such as one or more universal serial bus (USB) ports 860 (FIG. 12) as described herein or an RJ connector (e.g., for Ethernet communications), or slots for a data communications module or card (e.g., data communications module 570, FIG. 8), etc. The memory card (or memory card module) is inserted into a slot similar to slots 910-914, but located near the uppermost surface of the device 900, although the invention is not limited to this location. The packaging for sensors 930, 932 and 934 is shown in FIG. 13.

Figure 14C:
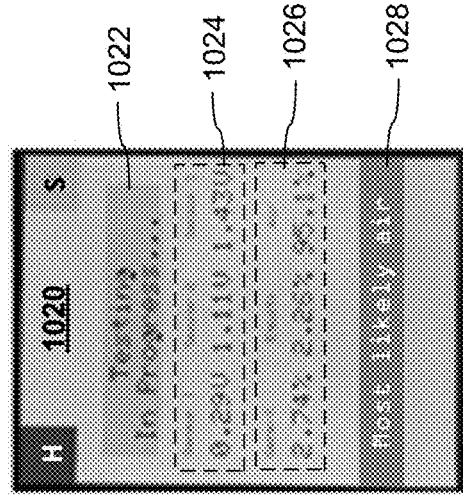
FIGS. 14A-F show exemplary screens for displaying certain information and receiving certain instructions from a user, in accordance with one or more embodiments of the present invention.
Figure 14B:
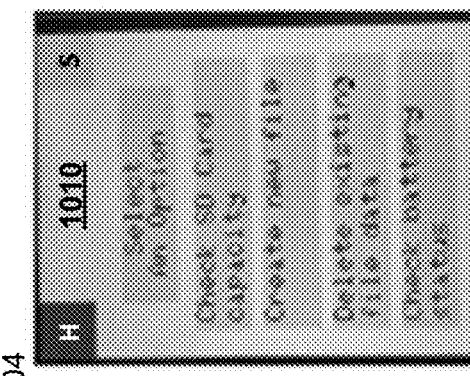
Figure 14A:
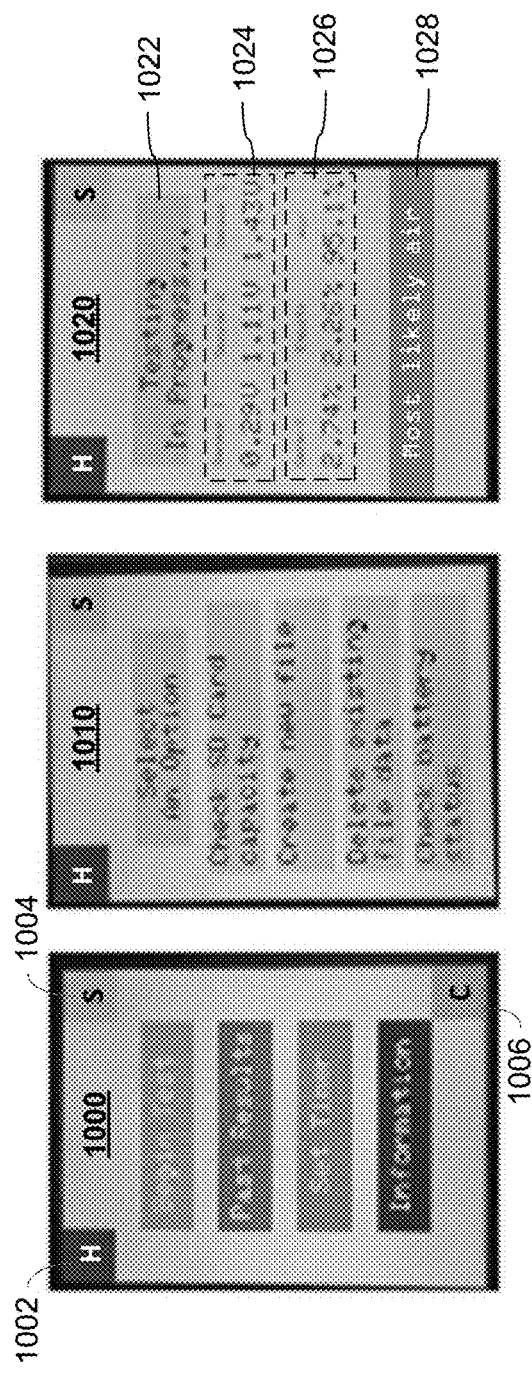
Figure 14F:
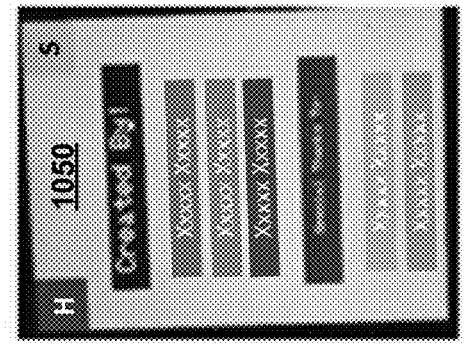

Various data and information that can be displayed on the display 920 is shown in FIGS. 14A-F. For example, FIG. 14A shows an initial or "home" menu 1000 that includes various selectable instructions (e.g., "Start test" and "Set timer"), parameters (e.g., "Information") and/or data (e.g., "Past results" and optionally "Information"). The menu 1000 is not limited to such items and examples, however. The regions in the corners labeled "H" 1002, "S" 1004 (which are also present in FIGS. 14B-F) and "C" may respectively represent links to the home menu 1000, a selectable function menu 1010 (FIG. 14B), and a credit screen 1050 (FIG. 14F). In some embodiments, the display may show a screen requiring login credentials (e.g., a user name and password) prior to displaying the home menu 1000.

The selectable function menu 1010 in FIG. 14B lists a plurality of different functions that can be carried out on or by the device 900, including checking the memory card capacity, creating a new file (e.g., for a new or different patient), deleting existing file data, and checking the battery status, although a subset of these functions may be displayed in some embodiments. Other functions that can be included in the selectable function menu 1010 may comprise the status of a wired or wireless connection to an external network, computer, server, etc., the resistance setting of any potentiometer or voltage divider (e.g., for calibration purposes), etc.

FIG. 14C shows a test screen 1020 that appears when the "Begin test" or "start test" instruction is selected in the home menu 1000 (FIG. 14A). The test screen 1020 in FIG. 14C may include a test status bar 1022 configured to display the status of the test (e.g., "warming up," "calibrating," "Ready—Press Button," "in progress," "Complete," etc.), the current voltage (or other measurable parameter reading) 1024 from each sensor, analytical data 1026 (e.g., regarding the VOC signature in the patient's breath sample), and a result bar 1028. The analytical data 1026 may include the probability that the sample tested includes a particular compound (e.g., acetone, ethanol, carbon dioxide, etc.) or is just air, the patient's estimated blood glucose level, etc. The result bar 1028 may give the most likely conclusion or result about the test, after the test reaches a sufficiently stable result (e.g., "Air," "Glucose too high," "Glucose too low," "Normal," "Inconclusive—test again," etc.).

Figure 14E:
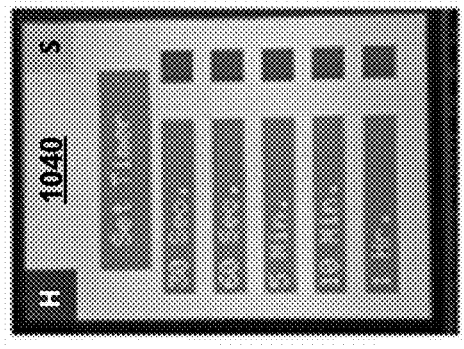
Figure 14D:
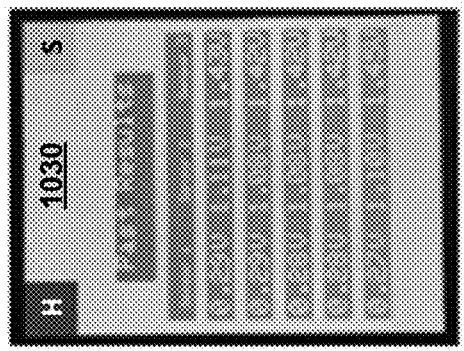

FIG. 14D shows a past results screen 1030 that appears when the "Past results" bar or button is selected in the home menu 1000 (FIG. 14A). The past results screen 1030 in FIG. 14D may display the n most recent test results in a particular data file or folder (e.g., for a particular patient), where n is an integer of at least 2 (e.g., 3 or more, 4-10, 5-8, etc.). Although the screen 1030 may display n rows of data, when there are less than n tests in the data file or folder, the remaining rows may appear blank. As shown in the past results screen 1030 in FIG. 14D, voltages from each sensor may be displayed, but alternatively (or additionally, on the same or a different screen), other data may be displayed, such as blood glucose level, concentrations of one or more VOCs, etc.

FIG. 14E shows a timer setting screen 1040 that appears when the "Set timer" bar or button is selected in the home menu 1000 (FIG. 14A). The past timer setting screen 1040 in FIG. 14E may display a plurality of different time lengths (e.g., 3 or more, 4-10, 5-8, etc.), and the user may select one of the time lengths for a reminder for one or more future (e.g., next) tests. In some embodiments, the timer is for a default function (e.g., either calibration or testing).

Figure 2:
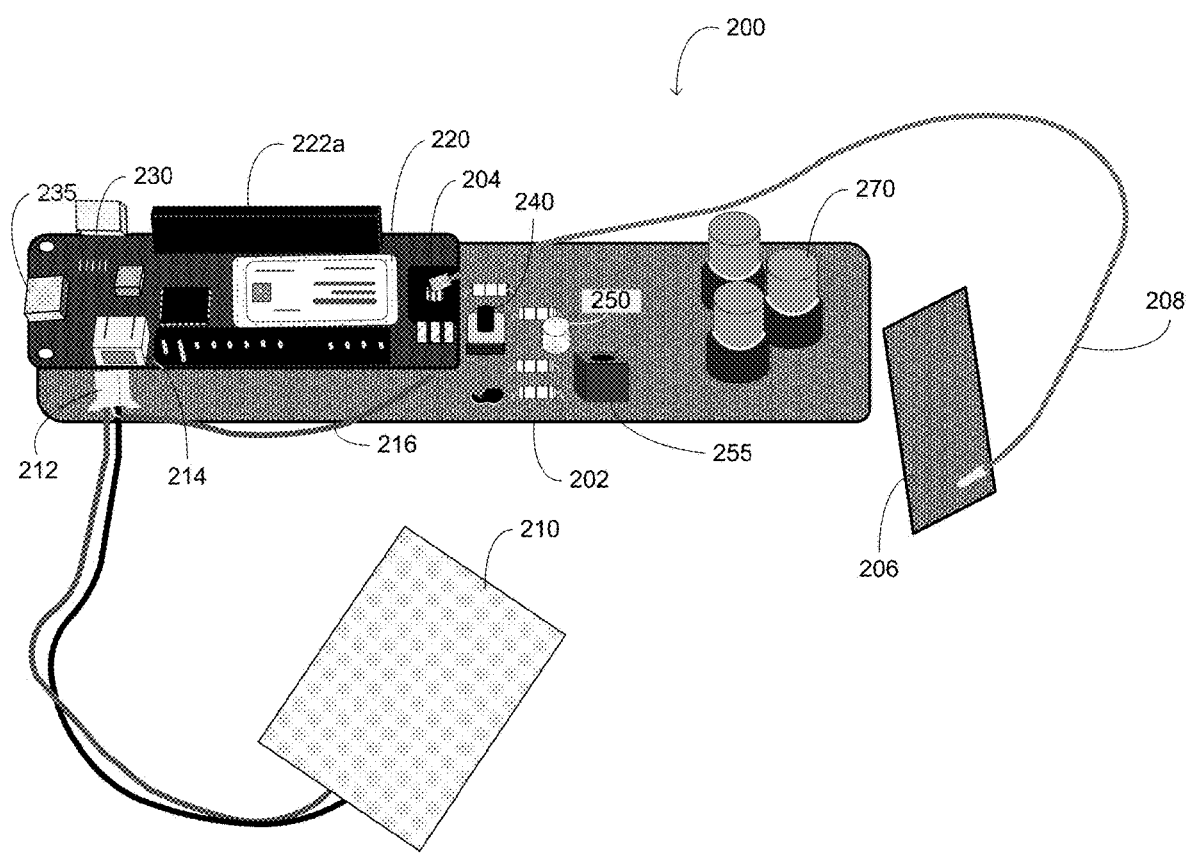
FIG. 2 is a photograph showing an exemplary circuit board, battery and antenna suitable for use in the present device.
Figure 3:
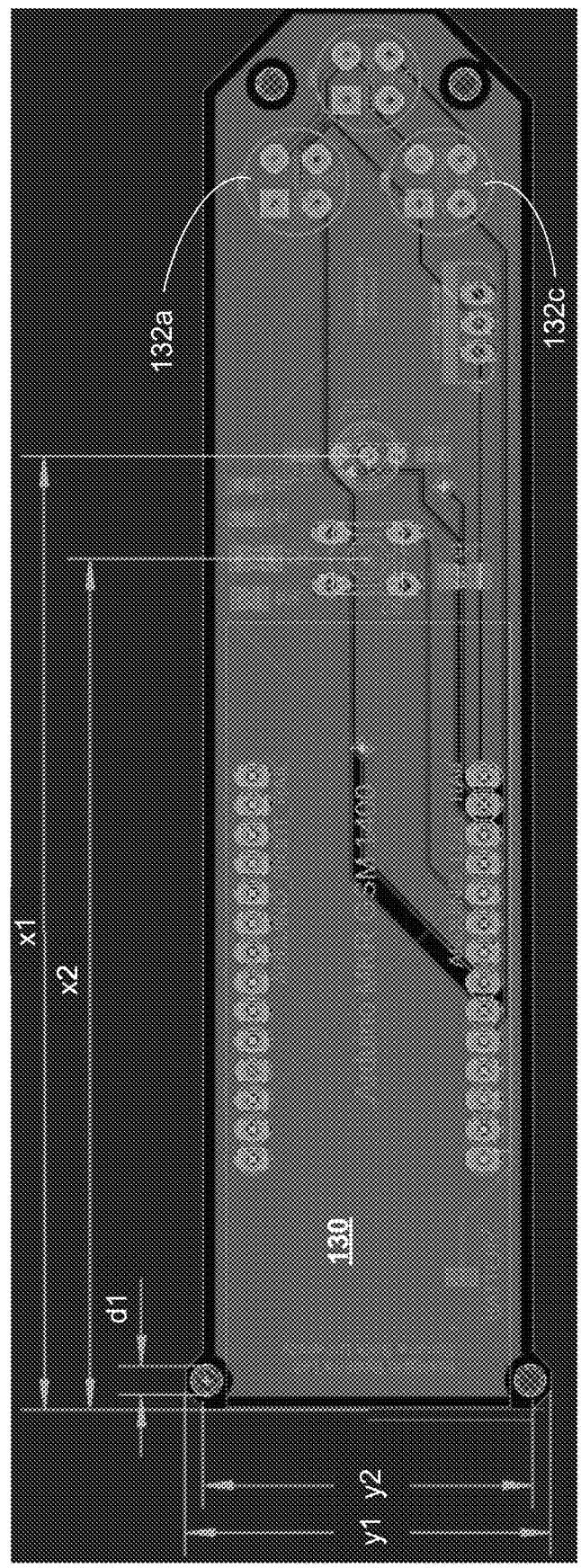
FIG. 3 is a schematic showing an exemplary circuit board layout suitable for use in the present device.

Referring back to FIG. 12, the circuit board 800 includes a sensor interfacing circuit 840 configured to transmit sensor data to and receive instructions and data (e.g., parametric setting data) from the microcontroller 830, a voltage regulator 850 that receives a stepped-down voltage from the battery 880 and that distributes one or more voltages to other components on the board 800, a USB connector 860 (as described herein), and a battery charging module 870. The sensor interfacing circuit 840 may comprise, for example, one or more of the ADCs on the board 200 of FIG. 2 or in the device 300 of FIGS. 5A-B, or the potentiometer 520 and the ADC 530 of FIG. 8, etc., and receives signals from the sensor(s) (not shown in FIG. 12) that detect the volatile analytes in the patient's breath 890. The sensor interfacing circuit 840 communicates with the microcontroller 830 through an ADC (not shown) as described herein. Similarly, the microcontroller 830 may send digital signals to the sensor interfacing circuit 840, and a DAC (also not shown) may convert some of the digital signals to analog signals for reception by the sensor interfacing circuit 840.

The battery 880 may be rechargeable, and receives a recharging voltage (e.g., 5 V) from an external source through the USB connector 860 and the battery charging module 870. The stepped-down voltage is less than the recharging voltage (e.g., 3.5 V), and is provided by the voltage regulator 850 to the microcontroller 830, the user interface 820, and the sensor interfacing circuit 840. The voltage regulator 850 may provide a stepped-up voltage greater than the stepped-down voltage (e.g., 5 V) to the memory card/module 810.

A further aspect of the present disclosure invention relates to algorithms, computer program(s), computer-readable media and/or software, implementable and/or executable in a computing device equipped with a digital signal processor, microprocessor or microcontroller, configured to perform one or more of the methods and/or one or more operations of the hardware disclosed herein. Thus, a further aspect of the invention relates to algorithms and/or software that create and/or implement part or all of any method disclosed herein. For example, the computer program or computer-readable medium generally contains a set of instructions which, when executed by an appropriate processing device (e.g., a signal processing device, such as a microcontroller, microprocessor or DSP device), is configured to perform the above-described method(s), operation(s), and/or algorithm(s).

The computer-readable medium may comprise any medium that can be read by a signal processing device configured to read the medium and execute code stored thereon or therein, such as a floppy disk, CD-ROM, magnetic tape or hard disk drive. Such code may comprise object code, source code and/or binary code. The code is generally digital, and is generally configured for processing by a conventional digital data processor (e.g., a microprocessor, microcontroller, or logic circuit such as a programmable gate array, programmable logic circuit/device or application-specific integrated circuit [ASIC]).

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A device, comprising:
    one or more metal oxide semiconductor (MOS) sensors configured to detect one or more volatile analytes in a person's breath and provide a parametric value representing a level or concentration of the one or more volatile analytes in the person's breath;
    a support vector machine or artificial neural network that correlates the parametric value with known levels or concentrations of a disease-related analyte in the person's blood:
    a microcontroller in communication with each of the one or more sensors, configured to receive the parametric value from each of the one or more sensors and execute the support vector machine or artificial neural network, the microcontroller containing logic adapted to correlate (i) the parametric value from the one or more sensors to the level or concentration of the disease-related analyte in the person's blood and/or (ii) the level or concentration of the one or more volatile analytes in the person's breath to the level or concentration of the disease-related analyte in the person's blood;
a transmitter configured to transmit at least one of the parametric value from each of the one or more sensors, the level or concentration of the one or more volatile analytes in the person breath, and/or the level or concentration of a disease-related analyte in the person's blood to at least one of an external processing device and a display;
a battery configured to provide electrical power to the one or more sensors, the microcontroller, and the transmitter; and
a housing that surrounds and/or encloses the one or more sensors, the microcontroller, the transmitter and the battery, or at least secures the one or more sensors, the microcontroller, the transmitter and the battery in place relative to one another, the housing containing or securing a tube or opening through which the person exhales so that the person's breath contacts the one or more sensors for a predetermined minimum period of time.

2. The device of claim 1, wherein the person has diabetes, and the disease-related analyte is glucose.

3. The device of claim 1, wherein the housing comprises a first chamber that encloses the one or more sensors, a second chamber that surrounds and/or encloses the microcontroller and the transmitter, and a wall, barrier or partition that separates the first chamber from the second chamber.

4. The device of claim 1, comprising a plurality of the sensors, each configured to detect (i) a different volatile analyte or (ii) at least one of the one or more of the volatile analytes in a different manner from the other sensor(s).

5. The device of claim 4, wherein the plurality of the sensors detect acetone, ethanol, methyl nitrate, isoprene, propane, benzene, methanol, ethyl benzene or carbon monoxide.

6. The device of claim 1, further comprising a user interface configured to communicate at least a status of the device to the person.

7. The device of claim 6, wherein the user interface comprises a light emitting diode (LED), a liquid crystal display (LCD), an electrochromic display or a touch screen.

8. The device of claim 1, further comprising (i) a port in the housing, configured to receive a voltage or current, and (ii) a battery recharging circuit, configured to receive the voltage or current and recharge the battery using the voltage or current.

9. The device of claim 1, further comprising a memory configured to store readings or outputs from each of the one or more sensors during testing of the person's breath.

10. A method of determining a level or concentration of a disease-related analyte in a person's blood, comprising:
a) the person exhaling through a tube or first opening in a housing of a device, the device containing one or more metal oxide semiconductor (MOS) sensors, and the housing being configured so that the person's breath contacts the one or more MOS sensors for a predetermined minimum period of time;
b) detecting one or more volatile analytes in the person's breath using the one or more MOS sensors,
c) providing a parametric value representing a level or concentration of the one or more volatile analytes in the person's breath from each of the one or more MOS sensors;
d) using a microcontroller in the housing and in communication with each of the one or more sensors, either:

i) determining the level or concentration of one or more volatile analytes in the person's breath, and correlating the level or concentration of the one or more volatile analytes in the person's breath to the level of concentration of the disease-related analyte in the person's blood; or
ii) correlating the parametric value from the one or more sensors to the level or concentration of the disease-related analyte in the person's blood,
wherein the microcontroller has been trained to correlate the levels or concentrations of the one or more volatiles analytes in the person's breath with known levels or concentrations of the disease-related analyte in the person's blood using a support vector machine or artificial neural network executable by the microcontroller; and
e) displaying the level or concentration of the disease-related analyte on a user interface.

11. The method of claim 10, further comprising transmitting the parametric value and/or the level or concentration of the disease-related analyte in a person's blood to at least one of an external data processing device and a display using a transmitter in the housing and in communication with the microcontroller.

12. The method of claim 10, wherein:
a) the housing comprises a first chamber that encloses the one or more sensors, a second chamber that surrounds and/or encloses the microcontroller and the transmitter, and a wall, barrier or partition that separates the first chamber from the second chamber, and
b) the tube or first opening is in fluid communication with the first chamber, and the method further comprises removing the person's breath from the first chamber of allowing the person's breath to pass through second opening in the first chamber.

13. The method of claim 10, wherein a plurality of the volatile analytes in the person's breath are determined using a plurality of the sensors, and each of the plurality of the sensors is configured to detect (i) a different volatile analyte or (ii) at least one of the one or more of the volatile analytes in a different manner from the other sensor(s).

14. The method of claim 13, wherein the person has diabetes, the disease-related analyte is glucose, the plurality of the sensors detect acetone and ethanol.

15. The method of claim 10, further comprising communicating at least a status of the device to the person using a user interface selected from a light emitting diode (LED), a liquid crystal display (LCD), an electrochromic display and a touch screen.

16. The method of claim 10, further comprising storing readings or outputs from each of the one or more sensors during testing of the person's breath in a memory in the device.

17. A non-transitory computer-readable medium, implementable and/or executable in a computing device equipped with a digital signal processor or microcontroller, containing a set of instructions which, when executed by the digital signal processor or microcontroller, is configured to perform the method of claim 10.

18. The device of claim 9, wherein the memory stores the support vector machine or artificial neural network, the memory is within the housing, and the support vector machine or artificial neural network is accessible and executable by the microcontroller.

19. The method of claim 10, further comprising loading a trained model on the microcontroller, wherein the trained model comprises the support vector machine or artificial neural network trained to detect and/or analyze patterns in (i) actual breath sample data, correlated to conventional measurements of the concentration of the disease-related analyte in the person's blood taken within an hour of the actual breath sample data, or (ii) data on simulated breaths containing low and high levels of the one or more volatile analytes.

20. The device of claim 1, wherein each of the one or more volatile analytes is a vapor or a gas, and each of the one or more MOS sensors directly detects the level or concentration of the vapor or the gas in the person's breath.

* * * * *